United States Patent
Brader

(10) Patent No.: US 10,588,949 B2
(45) Date of Patent: Mar. 17, 2020

(54) FACTOR IX POLYPEPTIDE FORMULATIONS

(71) Applicant: Bioverativ Therapeutics Inc., Waltham, MA (US)

(72) Inventor: Mark Brader, Lexington, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 624 days.

(21) Appl. No.: 14/776,125

(22) PCT Filed: Mar. 14, 2014

(86) PCT No.: PCT/US2014/029010
§ 371 (c)(1),
(2) Date: Sep. 14, 2015

(87) PCT Pub. No.: WO2014/144549
PCT Pub. Date: Sep. 18, 2014

(65) Prior Publication Data
US 2016/0000888 A1   Jan. 7, 2016

Related U.S. Application Data

(60) Provisional application No. 61/794,874, filed on Mar. 15, 2013.

(51) Int. Cl.
| | | |
|---|---|---|
| *A61K 38/36* | (2006.01) | |
| *A61K 38/48* | (2006.01) | |
| *A61K 9/00* | (2006.01) | |
| *A61K 9/19* | (2006.01) | |
| *A61K 47/02* | (2006.01) | |
| *A61K 47/10* | (2017.01) | |
| *A61K 47/22* | (2006.01) | |
| *A61K 47/26* | (2006.01) | |
| *A61M 5/158* | (2006.01) | |
| *A61M 5/178* | (2006.01) | |
| *A61M 5/19* | (2006.01) | |

(52) U.S. Cl.
CPC ........ *A61K 38/4846* (2013.01); *A61K 9/0019* (2013.01); *A61K 9/19* (2013.01); *A61K 47/02* (2013.01); *A61K 47/10* (2013.01); *A61K 47/22* (2013.01); *A61K 47/26* (2013.01); *A61M 5/158* (2013.01); *A61M 5/178* (2013.01); *A61M 5/19* (2013.01); *C12Y 304/21022* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,786,726 A | 11/1988 | Smith | |
| 5,981,285 A | 11/1999 | Carroll et al. | |
| 6,686,179 B2 | 2/2004 | Fleer et al. | |
| 6,730,328 B2 | 5/2004 | Maskiewicz et al. | |
| 7,112,580 B2 | 9/2006 | Raymond et al. | |
| 7,217,798 B2 | 5/2007 | Hinton et al. | |
| 7,348,004 B2 | 3/2008 | Peters et al. | |
| 7,404,956 B2 | 7/2008 | Peters et al. | |
| 7,566,565 B2 | 7/2009 | Peters et al. | |
| 7,592,010 B2 | 9/2009 | Rosen et al. | |
| 7,790,415 B2 | 9/2010 | Gillies et al. | |
| 8,367,805 B2 | 2/2013 | Chamberlain et al. | |
| 9,233,145 B2 | 1/2016 | Pierce et al. | |
| 9,623,091 B2 | 4/2017 | Pierce et al. | |
| 9,629,903 B2 | 4/2017 | Pierce et al. | |
| 9,670,475 B2 | 6/2017 | Pierce et al. | |
| 9,675,676 B2 | 6/2017 | Pierce et al. | |
| 2003/0203845 A1 | 10/2003 | Knudsen et al. | |
| 2005/0032174 A1 | 2/2005 | Peters et al. | |
| 2006/0128622 A1 | 6/2006 | Treuheit et al. | |
| 2007/0135343 A1* | 6/2007 | Webb .................. | A61K 9/0019 424/680 |
| 2009/0092582 A1 | 4/2009 | Bogin et al. | |
| 2009/0163699 A1 | 6/2009 | Chamberlain et al. | |
| 2009/0252720 A1 | 10/2009 | Ostergaard et al. | |
| 2009/0264627 A1 | 10/2009 | Gillies et al. | |
| 2010/0189682 A1 | 7/2010 | Schellenberger et al. | |
| 2010/0222554 A1 | 9/2010 | Weimer et al. | |
| 2010/0239554 A1 | 9/2010 | Schellenberger et al. | |
| 2011/0236412 A1 | 9/2011 | Drew | |
| 2012/0208759 A1 | 8/2012 | Fima et al. | |
| 2013/0171175 A1 | 7/2013 | Pierce et al. | |
| 2013/0202595 A1 | 8/2013 | Pierce et al. | |
| 2016/0000888 A1 | 1/2016 | Brader | |

(Continued)

FOREIGN PATENT DOCUMENTS

| | | |
|---|---|---|
| EP | 1942868 A2 | 7/2008 |
| EP | 2353588 A1 | 8/2011 |

(Continued)

OTHER PUBLICATIONS

Andersson, L.O., et al., "Purification and Characterization of Human Factor IX," Thrombosis Research 7(3):451-459, Pergamon Press, Inc., United States (Sep. 1975).

Burmeister, W.P., et al., "Crystal Structure of the Complex of Rat Neonatal Fc Receptor with Fc," Nature 372(6504):379-383, Nature Publishing Group, England (Nov. 1994).

Chang, C.W., et al., "Non-Ionic Amphiphilic Biodegradable PEG-PLGA-PEG Copolymer Enhances Gene Delivery Efficiency in Rat Skeletal Muscle," Journal of Controlled Release 118(2):245-253, Elsevier B.V., Netherlands (Apr. 2007).

Ewenstein, B.M., et al., "Pharmacokinetic Analysis of Plasma-derived and Recombinant F IX Concentrates in Previously Treated Patients with Moderate or Severe Hemophilia B," Transfusion 42:190-197, American Association of Blood Banks, United States (Feb. 2002).

Kisker, C.T., et al., "Prophylaxis in Factor IX Deficiency Product and Patient Variation," Haemophilia 9(3):279-284, Blackwell Publishing Ltd., England (May 2003).

(Continued)

*Primary Examiner* — Michael Szperka
(74) *Attorney, Agent, or Firm* — Lathrop GPM LLP; James H. Velema, Esq.

(57) ABSTRACT

The present invention provides formulations comprising a Factor IX-FcRn Binding Partner (FIXFBP) polypeptide, and methods of administering FIXFBP.

42 Claims, No Drawings

Specification includes a Sequence Listing.

(56) References Cited

U.S. PATENT DOCUMENTS

| | | | |
|---|---|---|---|
| 2016/0166657 A1 | 6/2016 | Pierce et al. | |
| 2016/0243206 A1 | 8/2016 | Pierce et al. | |
| 2016/0257943 A1 | 9/2016 | Pierce et al. | |
| 2016/0346365 A1 | 12/2016 | Pierce et al. | |
| 2017/0021022 A1 | 1/2017 | Webb et al. | |
| 2017/0173122 A1* | 6/2017 | Thome | F26B 5/06 |
| 2018/0002684 A1 | 1/2018 | Pierce et al. | |

FOREIGN PATENT DOCUMENTS

| | | | | |
|---|---|---|---|---|
| WO | WO-9726909 A1 * | 7/1997 | | A61K 9/0019 |
| WO | WO-9816250 A1 | 4/1998 | | |
| WO | WO-9835689 A1 | 8/1998 | | |
| WO | WO-0240544 A2 | 5/2002 | | |
| WO | WO-03020764 A2 | 3/2003 | | |
| WO | WO-2004101740 A2 | 11/2004 | | |
| WO | WO-2005001025 A2 | 1/2005 | | |
| WO | WO-2005058283 A2 | 6/2005 | | |
| WO | WO 2005/089712 A1 | 9/2005 | | |
| WO | WO-2007053533 A2 | 11/2005 | | |
| WO | WO-2006074199 A1 | 7/2006 | | |
| WO | WO-2007090584 A1 | 8/2007 | | |
| WO | WO-2007103515 A2 | 9/2007 | | |
| WO | WO-2007115724 A2 | 10/2007 | | |
| WO | WO-2007144173 A1 | 12/2007 | | |
| WO | WO-2007149406 A2 | 12/2007 | | |
| WO | WO-2008022151 A1 | 2/2008 | | |
| WO | WO-2008118507 A2 | 10/2008 | | |
| WO | WO-2009023270 A2 | 2/2009 | | |
| WO | WO-2009051717 A2 | 4/2009 | | |
| WO | WO-2009130198 A2 | 10/2009 | | |
| WO | WO-2009130602 A2 | 10/2009 | | |
| WO | WO-2009137254 A2 | 11/2009 | | |
| WO | WO-2009140015 A2 | 11/2009 | | |
| WO | WO-2010020690 A1 | 2/2010 | | |
| WO | WO-2010091122 A1 | 8/2010 | | |
| WO | WO-2012006624 A2 * | 1/2012 | | A61K 38/4846 |
| WO | WO-2014052490 A1 * | 4/2014 | | C07K 14/745 |
| WO | WO-2014144549 A1 | 9/2014 | | |

OTHER PUBLICATIONS

Lambert, C. and Prange, R., "Posttranslational N-glycosylation of the Hepatitis B Virus Large Envelope Protein," Virology Journal 4:45, BioMed Central Ltd., England, 9 pages (May 2007).

Martinowitz, U., et al., "Pharmacokinetic Properties of IB1001, an Investigational Recombinant Factor IX, in Patients with Haemophilia B: Repeat Pharmacokinetic Evaluation and Sialylation Analysis," Haemophilia 18(6):881-887, Blackwell Publishing Ltd., England (Nov. 2012).

Negrier, C., et al., "Enhanced Pharmacokinetic Properties of a GlycoPEGylated Recombinant Factor IX: A First Human Dose Trial in Patients with Hemophilia B," Blood 118(10):2695-2701, The American Society of Hematology, United States (Sep. 2011).

Ragni, M.V., et al., "Use of Recombinant Factor IX in Subjects with Haemophilia B Undergoing Surgery," Haemophilia 8(2):91-97, Blackwell Science, England (Mar. 2002).

Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (Dec. 1994).

International Search Report and Written Opinion of the International Searching Authority dated Jul. 18, 2014 for International Application No. PCT/US14/29010 filed Mar. 14, 2014.

Ahnstrom, J., et al., "A 6-year Follow-Up of Dosing, Coagulation Factor Levels and Bleedings in Relation to Joint Status in the Prophylactic Treatment of Haemophilia," Haemophilia 10(6):689-697, Blackwell Publishing Ltd., England (2004).

Armour, K.L., et al., "Recombinant Human IgG Molecules Lacking Fcγ Receptor I Binding and Monocyte Triggering Activities," European Journal of Immunology 29(8):2613-2624, Wiley-VCH, Germany (1999).

Beal, S.L., "Ways to Fit a PK Model with Some Data Below the Quantification Limit," Journal of Pharmacokinetics and Pharmacodynamics 28(5):481-504, Plenum Publishing Corporation, United States (2001).

Bergstrand, M. and Karlsson, M.O., "Handling Data Below the Limit of Quantification in Mixed Effect Models," The AAPS Journal 11(2):371-380, American Association of Pharmaceutical Scientists, United States (2009).

Bjorkman, S., and Ahlen, V., et al., "Population Pharmacokinetics of Plasma-Derived Factor IX in Adult Patients with Haemophilia B: Implications for Dosing in Prophylaxis," European Journal of Clinical Pharmacology 68(6):969-977, Springer-Verlag, Germany (2012).

Bjorkman, S. and Berntorp, E., "Pharmacokinetics of Coagulation Factors: Clinical Relevance for Patients with Haemophilia," Clinical Pharmacokinetics 40(11):815-832, Adis International Ltd., New Zealand (2001).

Bjorkman, S., et al., "Pharmacokinetics of Factor IX in Patients With Haemophilia B. Methodological Aspects and Physiological Interpretation," European Journal of Clinical Pharmacology 46(4):325-332, Springer-Verlag, Germany (1994).

Bjorkman, S., et al., "Pharmacokinetics of Recombinant Factor IX in Relation to Age of the Patient: Implications for Dosing in Prophylaxis," Haemophilia 7(2):133-139, Blackwell Science Ltd., England (2001).

Bjorkman, S., "Population Pharmacokinetics of Recombinant Factor IX: Implications for Dose Tailoring," Haemophilia 19(5):753-757,John Wiley & Sons Ltd., England (2013).

Bjorkman, S., "Prophylactic Dosing of Factor VIII and factor IX from a Clinical Pharmacokinetic Perspective," Haemophilia 9(1):101-110, Blackwell Publishing Ltd., England (2003).

Brendel, K., et al., "Are Population Pharmacokinetic and/or Pharmacodynamic Models Adequately Evaluated? A Survey of the Literature from 2002 to 2004," Clinical Pharmacokinetics 46(3):221-234,Adis Data Information BV, New Zealand (2007).

Brinkhous, K.M., et al., "Recombinant Human Factor IX: Replacement Therapy, Prophylaxis, and Pharmacokinetics in Canine Hemophilia B," Blood 88(7):2603-2610, The American Society of Hematology, United States (1996).

Brutlag, D.L., et al., "Improved Sensitivity of Biological Sequence Database Searches," Computer Applications in the Biosciences 6(3):237-245, Oxford University Press, England (1990).

Byon, W., et al., "Establishing Best Practices and Guidance in Population Modeling: an Experience with an Internal Population Pharmacokinetic Analysis Guidance," CPT: Pharmacometrics & Systems Pharmacology 2:e51:1-8, ASCPT, United States (2013).

Carlsson, M., et al., "Multidose Pharmacokinetics of Factor IX: Implications for Dosing in Prophylaxis," Haemophilia 4(2):83-88, Blackwell Publishing Ltd., England (1998).

Chang, L.C., et al., "Sustained Release of Transgenic Human Factor IX: Preparation, Characterization, and in Vivo Efficacy," Molecular Pharmaceutics 8(5):1767-1774, American Chemical Society, United States (2011).

Chitlur, M., et al, "Inhibitors in Factor IX Deficiency a Report of the ISTH-SSC International FIX Inhibitor Registry (1997-2006)," Haemophilia 15(5):1027-1031, Blackwell Publishing Ltd., England (2009).

Collins, P., et al., "Break-Through Bleeding in Relation to Predicted Factor VIII Levels in Patients Receiving Prophylactic Treatment for Severe Hemophilia A," Thrombosis and Haemostasis 7(3):413-420, Blackwell Publishers, England, (2009).

Notice of Allowance dated Aug. 14, 2017 in U.S. Appl. No. 14/982,934, inventors Pierce, G., et al., filed Dec. 29, 2015, 13 pages.

Döbeli, H., et al., "Role of the Carboxy-Terminal Sequence on the Biological Activity of Human Immune Interferon (IFN-γ)," Journal of Biotechnology 7:199-216, Elsevier Science Publishers B.V., Netherlands (1988).

Dimichele, D., "Inhibitor Development in Haemophilia B: an Orphan Disease in Need of Attention," British Journal of Haematology 138(3):305-315, Blackwell Publishing Ltd., England (2007).

(56) References Cited

OTHER PUBLICATIONS

Dimichele, D., "Inhibitors: Resolving Diagnostic and Therapeutic Dilemmas," Haemophilia 8(3):280-287, Blackwell Science Ltd., England (2002).
Dumont, J.A., et al., "Monomeric Fc Fusion Molecules," in Therapeutic Monoclonal Antibodies from Bench to Clinic, Chapter 33, pp. 779-795, John Wiley & Sons., Inc., United States (2009).
Dumont, J.A., et al., "Monomeric Fc Fusions: Impact on Pharmacokinetic and Biological Activity of Protein Therapeutics," BioDrugs 20(3):151-160, Springer International, New Zealand (2006).
Ette, E.I. and Ludden, T.M., "Population Pharmacokinetic Modeling: the Importance of Informative Graphics," Pharmaceutical Research 12(12):1845-1855, Plenum Publishing Corporation, United States (1995).
Extended European Search Report for Application No. EP 13842864.4, Munich, Germany, dated Apr. 11, 2016, 8 pages.
Food and Drug Administration, "Guidance for Industry on Population Pharmacokinetics; Availability," Federal Register 64(27):6663-6664, Food and Drug Administration, HHS, United States (1999).
Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).
Gayle, R.B., III., et al., "Identification of Regions in Interleukin-1α Important for Activity," The Journal of Biological Chemistry 268(29):22105-22111, The American Society for Biochemistry and Molecular Biology, Inc., United States (1993).
Giangrande, P., "Haemophilia B: Christmas Disease," Expert Opinion on Pharmacotherapy 6(9):1517-1524, Ashley Publications Ltd., England (2005).
Gillis, S., et al., "γ-Carboxyglutamic Acids 36 and 40 do not Contribute to Human Factor IX Function," Protein Science 6(1):185-196, Wiley-Blackwell, United States (1997).
Gui, T., et al., "Circulating and Binding Characteristics of Wild-type Factor IX and Certain Gla Domain Mutants in Vivo," Blood 100(1):153-158, American Society of Hematology, United States (2002).
Hansson, K. and Stenflo, J., "Post-Translational Modifications in Proteins Involved in Blood Coagulation," Journal Thrombosis and Haemostasis 3(12):2633-2648, Blackwell Pub., England (2005).
Huang, C., "Receptor-Fc Fusion Therapeutics, Traps, and Mimetibody Technology," Current Opinion in Biotechnology 20(6):692-699, Current Biology, England (2009).
International Search Report and Written Opinion for Application No. PCT/US2011/043569, ISA/US, Alexandria, Virginia, United States, dated Feb. 14, 2012, 11 pages.
International Search Report and Written Opinion for Application No. PCT/US2013/061747, ISA/US, Alexandria, Virginia, United States, dated Dec. 16, 2013, 9 pages.
Jonsson, E.N. and Karlsson, M.O., "Xpose—an S-plus Based Population Pharmacokinetic/pharmacodynamic Model Building Aid for NONMEM," Computer Methods and Programs in Biomedicine 58(1):51-64, Elsevier Science Ireland Ltd., Ireland (1999).
Karlsson, M.O. and Sheiner, L.B., "The Importance of Modeling Interoccasion Variability in Population Pharmacokinetic Analyses," Journal of Pharmacokinetics and Biopharmaceutics 21(6):735-750, Plenum Publishing Corporation, United States (1993).
Kiang, T.K.L., et al., "Fundamentals of Population Pharmacokinetic Modelling, Modelling and Software," Clinical Pharmacokinetics 51(8):515-525, Springer International Publishing AG, New Zealand (2012).
Kuo, T.T. and Aveson, V.G., "Neonatal Fc Receptor and IgG-based Therapeutics," MAbs 3(5):422-430, Taylor & Francis, United States (2011).
Lindbom, L., et al., "Perl-speaks-NONMEM (PsN)—a Perl Module for NONMEM Related Programming," Computer Methods and Programs in Biomedicine 75(2):85-94,Elsevier Ireland Ltd., Ireland (2004).
Mahmood, I., "Theoretical Versus Empirical Allometry: Facts Behind Theories and Application to Pharmacokinetics," Journal of Pharmaceutical Sciences 99(7):2927-2933,Wiley-Liss, Inc. and the American Pharmacists Association, United States (2010).
Mannucci, P.M. and Tuddenham, E.G., "The Hemophilias—from Royal Genes to Gene Therapy," The New England Journal of Medicine 344(23):1773-1779, Massachusetts Medical Society, United States (2001).
"MASAC Recommendations Concerning Products Licensed for the Treatment of Hemophilia and Other Bleeding Disorders," Hemophilia. org, accessed at http://www.hemophilia.org/Researchers-Healthcare-Providers/Medical-and-Scientific-Advisory-Council-MASAC/All-MASAC-Recommendations/Recommendations-Concerning-Products-Licensed-for-the-Treatment-of-Hemophilia-and-Other-Bleeding-Disorders, accessed on Sep. 8, 2014, 37 pages.
McCarthy, K., et al., "Pharmacokinetics of Recombinant Factor IX After Intravenous and Subcutaneous Administration in Dogs and Cynomolgus Monkeys," Thrombosis and Haemostasis 87(5):824-830, Schattauer GmbH, Stuttgart, Germany (2002).
Mei, B., et al., "Expression of Human Coagulation Factor VIII in a Human Hybrid Cell Line, HKB11," Molecular Biotechnology 34(2):165-178, Humana Press Inc., United States (2006).
Neumann, E., et al., "Gene Transfer into Mouse Lyoma Cells by Electroporation in High Electric Fields," The EMBO Journal 1(7):841-845, IRL Press Limited, England (1982).
Nilsson, I.M., et al., "Twenty-Five Years' Experience of Prophylactic Treatment in Severe haemophilia A and B," Journal of Internal Medicine 232(1):25-32, Blackwell Scientific Publications, England (1992).
Oganesyan, V., et al., "Structural Characterization of a Human Fc Fragment Engineered for Extended Serum Half-Life," Molecular Immunology 46(8-9):1750-1755, Pergamon Press, England (2009).
Page, D., "The Blood Factor: Breakthrough in Factor IX Products, Canadian Study Results Point to Importance of Early Prophylaxis," Hemophilia Today 45(3):29, Canadian Hemophilia Society, Canada (Nov. 2010).
Peters, R., Abstract entitled "Enhanced Pharmacokinetics of Factor IX as a Monomeric Fc Fusion," 2007 J. Throm. & Haemostasis S2(5):O-M-001—O-M-096 at O-M-016, 1 page.
Peters, R., Slides entitled "Enhanced Pharmacokinetics of Factor IX as a Monomeric Fc Fusion Protein," presented to the International Society on Thrombosis and Haemostasis Jul. 9, 2007, 14 pages.
Peters, R., Slides entitled "*Improved Pharmacokinetics of Factor IX as a Monomeric Fc Fusion Protein*," presented at National Hemophilia Foundation Workshop Mar. 30, 2006, 11 pages.
Reagan-Shaw, S., et al., "Dose Translation from Animal to Human Studies Revisited," Federation of American Societies for Experimental Biology Journal 22(3):659-661, The Federation, United States (2008).
Ron, D., et al., "Expression of Biologically Active Recombinant Keratinocyte Growth Factor: Structure/Function Analysis of Amino-Terminal Truncation Mutants," The Journal of Biological Chemistry 268(4):2984-2988, American Society for Biochemistry and Molecular Biology, United States (1993).
Roopenian, D.C. and Akilesh, S., "FcRn: the Neonatal Fc Receptor Comes of Age," Nature Reviews Immunology 7(9):715-725, Nature Publishing Group, England (2007).
Roth, D.A., et al., "Human Recombinant Factor IX: Safety and Efficacy Studies in Hemophilia B Patients Previously Treated with Plasma-Derived Factor IX Concentrates," Blood 98(13):3600-3606, The American Society of Hematology, United States (2001).
Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (1995).
Savic, R.M. and Karlsson, M.O., "Importance of Shrinkage in Empirical Bayes Estimates for Diagnostics: Problems and Solutions," The AAPS Journal 11(3):558-569, American Association of Pharmaceutical Scientists, United States (2009).
Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).

(56) References Cited

OTHER PUBLICATIONS

Schulte, S., "Half-life Extension Through Albumin Fusion Technologies," Thrombosis Research 124(Suppl. 2):S6-S8, Pergamon Press, United States (2009).
Screenshot of "Special Issue: Abstracts of XXIXth International Congress of the World Federation of Hemophilia, Buenos Aires, Argentina, Jul. 10-14, 2010," Haemophilia 16(Suppl. 4):1-170.
Shapiro, A.D., et al., "Abstracts of the XXIXth International Congress of the World Federation of Hemophilia," Haemophilia 16(Suppl. 4):1-158, Abstract 07FP07 at 30, Buenos Aires, Argentina, Jul. 10-14, 2010.
Shapiro, A.D., et al., "The Safety and Efficacy of Recombinant Human Blood Coagulation Factor IX in Previously Untreated Patients with Severe or Moderately Severe Hemophilia B," Blood 105(2):518-525, American Society of Hematology, United States (2005).
Shapiro, A.D., et al., "Use of Pharmacokinetics in the Coagulation Factor Treatment of Patients with Haemophilia," Haemophilia 11(6):571-582, Blackwell Publishing Ltd., England (2005).
Shapiro, A.D., "Recombinant factor IX-Fc fusion protein (rFIXFc) demonstrates safety and prolonged activity in a phase 1/2a study in hemophilia B patients," Blood 119(3):666-672, The American Society of Hematology, United States (2012).
Sherwin, C.M.T., et al., "Fundamentals of Population Pharmacokinetic Modelling, Validation Methods," Clinical Pharmacokinetics 51(9):573-590, Springer International Publishing AG, New Zealand (2012).
Shields, R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604, American Society for Biochemistry and Molecular Biology, United States (2001).
Srivastava, A., et al., "Guidelines for the Management of Hemophilia," Haemophilia 19(1):e1-e47, Blackwell Publishing Ltd., England (2013).
Summary of Product Characteristics for Benefixtm, Electronic Medicines Compendium, medicines.org.uk, accessed at http://www.medicines.org.uk/emc/medicine/20376/SPC/BENEFIXTtm/#PHARMACODYNAMICPROPS, accessed on Sep. 16, 2014, 11 pages.
Supplementary European Search Report for Application No. EP11804476, Munich, Germany, dated Mar. 5, 2014, 6 pages.
Vaccaro, C., et al., "Engineering the Fc region of Immunoglobulin G to Modulate in vivo Antibody Levels," Nature Biotechnology 23(10):1283-1288, Nature America Publishing, United States (2005).
Wade, J.R., et al., "A Guide for Reporting the Results of Population Pharmacokinetic Analyses: a Swedish Perspective," The AAPS Journal 7(2):45:E456-E460, American Association of Pharmaceutical Scientists, United States (2005).
Wang, D.D., et al., "Fixed Dosing Versus Body Size-Based Dosing of Monoclonal Antibodies in Adult Clinical Trials," The Journal of Clinical Pharmacology 49(9):1012-1024, American College of Clinical Pharmacology, United States (2009).
Ward, E.S. and Ghetie, V., "The Effector Functions of Immunoglobulins: Implications for Therapy," Therapeutic Immunology 2(2):77-94, Blackwell Science Ltd., England (1995).
White, G.C. II., et al., "Recombinant Factor IX," Thrombosis and Haemostasis 78(1):261-265, F.K. Schattauer Verlagsgesellsehaft mbH, Germany (1997).
White, G.C. II., et al., "Variability of in Vivo Recovery of Factor IX after Infusion of Monoclonal Antibody Purified Factor IX Concentrates in Patients with Hemophilia B. The Mononine Study Group," Thrombosis and Haemostasis 73(5):779-784, Stuttgart, Schattauer, Germany (1995).
Wigler, M., et al., "Biochemical Transfer of Single-Copy Eucaryotic Genes Using Total Cellular DNA as Donor," Cell 14(3):725-731, Cell Press, United States (1978).
Xu, X.S., et al., "Shrinkage in Nonlinear Mixed-effects Population Models: Quantification, Influencing Factors, and Impact," The AAPS Journal 14(4):927-936, American Association of Pharmaceutical Scientists, United States (2012).

Hansen, L., et al., "The pharmacokinetics of a long-acting Factor IX (40K PEG-RFIX) in minipigs suggests at least a once-weekly dosing regime," Journal of Thrombosis and Haemostasis 7(Suppl. 2): 134, International Society on Thrombosis and Haemostasis, England, Abstract OC-MO-085 (2009).
Shapiro, A.D., et al., "Safety and prolonged biological activity following a single administration of a recombinant molecular fusion of native human coagulation factor IX and the Fc region of immunoglobulin G (IgG) (rFIXFc) to subjects with hemophilia B," Haemophilia 16(Suppl. 4): 30, Blackwell Publishing Ltd., United Kingdom, Abstract 07FP07 (Jul. 2010).
U.S. Food and Drug Administration, "Highlights of Prescribing Information, ALPROLIX," revised Mar. 2014.
Communication pursuant to Rule 114(2) EPC, dated Oct. 30, 2015, Third Party Observations (Article 115 EPC) for Application No. EP11804476.7, European Patent Office, Germany.
Ezban, M., et al., "Pharmacokinetic (PK) and pharmacodynamics (PD) properties of a new recombinant long acting factor IX (40KPEG-RFIX) product after intravenous (IV) administration to hemophilia B dogs," PP-TH-579, Poster Presentation, Journal of Thrombosis and Haemostasis 7(Suppl. 2): 1-1204:134, International Society on Thrombosis and Haemostasis, United States (Jun. 2009).
Ezban, M., et al., "Pharmacokinetic (PK) and pharmacodynamics (PD) properties of a new recombinant long acting factor IX (40KPEG-RFIX) product after intravenous (IV) administration to hemophilia B (HB) dogs," PP-TH-579, Poster Presentation, presented at XXII Congress of the International Society of Thrombosis and Haemostasis, Boston, MA, USA, Jul. 11-16, 2009.
National Hemophilia Foundation, "Hemophilia B," hemophilia.org, accessed at https://www.hemophilia.org/Bleeding-Disorders/Types-of-Bleeding-Disorders/Hemophilia-B, accessed on Mar. 4, 2014, 2 pages.
Peters, R., Abstract entitled "Enhanced Pharmacokinetics of Factor IX as a Monomeric Fc Fusion," 2007 J. Throm. & Haemostasis S2(5):O-M-001—O-M-096 at O-M-016, 1 pages.
White, G.C. II., et al., "Scientific and Standardization Committee Communication, Definitions in Hemophilia, Recommendation of the Scientific Subcommittee on Factor VIII and Factor IX of the Scientific and Standardization Committee of the International Society on Thrombosis and Haemostasis" Thromb Haemost 85:560, Schattauer GmbH, Germany (2001).
Metzner, H.J., et al., "Genetic fusion to albumin improves the pharmacokinetic properties of factor IX," Thrombosis and Haemostasis 102(4):634-644, Stuttgard, Schattauer, Germany (2009).
Assignment from inventors to applicant, 3 pages.
Avonex label (Suppl-5008) downloaded from: https://www.accessdata.fda.gov/scripts/cder/daf/index.cfm?event=overview.process&applno=103628, 23 pages.
Benefix (reformulated) US prescribing information, http://labeling.pfizer.com/showlabeing.aspx?id=492, 24 pages.
Buschle et al. (1953) "A compatible Solution for Administration with Blood," Anesthesiology 14:53-59.
Chai et al. (1995) "Effects of Erythrocyte Aggregation and Blood Coagulation from Iohexol Solutions with an Without Sodium Chloride," Acta Radiologica, 36:204-209.
Chient et al., (1973) "Ultravascular Basis of the Mechanism of Rouleaux Formation," Microvascular Research, 5:155-166.
Constantino et al., (2004) Lyophilization of Biopharmaceuticals, 197-198.
Corry et al., (1983) "Action of hydryxyethyl starch on the flow properties of human erythrocyte suspensions," Biorheology, 20:705-717.
Extract from the USPTO patent Assignment database for records relating to the priority U.S. Appl. No. 60/732,221, 4 pages.
International Blood/Plasma News, 18(9):127, 2001.
Notice of Opposition to European Patent No. 1 942 868 B1, dated Jan. 19, 2018, 19 pages.
Powell et al. (2005) "A new formulation of recombinant human factor IX is Bioequivalent to BeneFIX: A Double-Blind, Randomized, Crossover Pharmacokinetic and Open-Label Safety and Efficacy Study," Blood, 106(11):4076.
Reply of Patent Proprietor to Notice of Opposition for European Patent No. 1 942 868 B1, dated Jun. 14, 2018, 23 pages.

(56) References Cited

OTHER PUBLICATIONS

Simulect label downloaded at: https://www.accessdata.fda.gov/scripts/cder/daf/index.cfm?event=overview.process&applno=103764.
Stranz, Marc, "The Implications of Osmolality, Osmolarity and pH in Infusion Therapy," INS Annual Conference (2005), pp. 1-5.
Summary of Product Characteristics, published with EMA Marketing Authorization for BeneFIX on Aug. 27, 1997, 57 pages.
Summons to Attend Oral Proceedings and Annex to the Communication, for European Patent Application No. 06827036.2, dated Oct. 8, 2018, 10 pages.
Thyrogen label downloaded at: https://www.accessdata.fda.gov/scripts/cder/daf/index.cfm?event=overview.process&applno=020898.
van den Berg et al., (2000) "BeneFix induces agglutination of red cells; is there a clinical relevance and can it be prevented?," Blood, 96(11):Part 1:641a.
Grounds for Appeal in connection with opposition against European Patent No. 1942868 / Application No. 06827036.2 filed Nov. 15, 2019 (37 pages).
Florence et al., Physicochemical Principles of Pharmacy, $2^{nd}$ Ed., The MacMillan Press Ltd., 1988, doi: 10.1007/978-1-349-16558-2.
Wyeth Biopharma, BeneFIX Circular, "BeneFIX Coagulation Factor IX (Recombinant)", Sep. 13, 2006.
Declaration of Marc Stranz (Grounds for Appeal—D24, 5 pages).
Marc Stranz, Curriculum Vitae (Grounds for Appeal—D24a Exhibit A, 4 pages).

* cited by examiner

SEQUENCE LISTING

<160> NUMBER OF SEQ ID NOS: 4

<210> SEQ ID NO 1
<211> LENGTH: 7583
<212> TYPE: DNA
<213> ORGANISM: Artificial Sequence
<220> FEATURE:
<223> OTHER INFORMATION: FIX-Fc Chain

<400> SEQUENCE: 1

```
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgaccccgc ccattgacgt caataatgac gtatgttccc atagtaacgc     180
caatagggac tttccattga cgtcaatggg tggagtattt acggtaaact gcccacttgg     240
cagtacatca agtgtatcat atgccaagta cgccccctat tgacgtcaat gacggtaaat     300
ggcccgcctg gcattatgcc cagtacatga ccttatggga ctttcctact tggcagtaca     360
tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta taagcagag ctctctggc     600 taactagaga acccactgct tactggctta tcgaaattaa tacgactcac tatagggaga     660
cccaagcttc gcgacgtacg gccgccacca tgcagcgcgt gaacatgatc atggcagaat     720
caccaggcct catcaccatc tgccttttag gatatctact cagtgctgaa tgtacaggtt     780
tgtttccttt tttaaaatac attgagtatg cttgcctttt agatatagaa atatctgatg     840
ctgtcttctt cactaaattt tgattacatg atttgacagc aatattgaag agtctaacag     900
ccagcacgca ggtggtaag tactgtggga acatcacaga ttttggctcc atgccctaaa     960
gagaaattgg ctttcagatt atttggatta aaaacaaaga cttttcttaag agatgtaaaa    1020 ttttcatgat gttttctttt ttgctaaaac taaagaatta ttcttttaca tttcagtttt    1080
tcttgatcat gaaaacgcca acaaaattct gaatcggcca agagaggtata attcaggtaa    1140 attggaagag tttgttcaag ggaatctaga gagagaatgt atggaagaaa agtgtagttt    1200
tgaagaagca cgagaagttt ttgaaaacac tgaaagaaca actgaatttt ggaagcagta    1260
tgttgatgga gatcagtgtg agtccaatcc atgtttaaat ggcggcagtt gcaaggatga    1320
cattaattcc tatgaatgtt ggtgtccctt tggatttgaa ggaagaact gtgaattaga    1380 tgtaacatgt aacattaaga atggcagatg cgagcagttt tgtaaaaata gtgctgataa    1440
caaggtggtt tgctcctgta ctgagggata tcgacttgca gaaaaccaga gtcctgtga    1500 accagcagtg ccatttccat gtggaagagt ttctgtttca caacttcta agctcacccg    1560 tgctgagact gtttttcctg atgtggacta tgtaaattct actgaagctg aaaccatttt    1620
ggataacatc actcaaagca cccaatcatt taatgacttc actcggggttg ttggtggaga    1680 agatgccaaa ccaggtcaat tcccttggca ggttgttttg aatggtaaag ttgatgcatt    1740
ctgtggaggc tctatcgtta tgaaaaatg gattgtaact gctgcccact gtgttgaaac    1800
tggtgttaaa attacagttg tcgcaggtga acataatatt gaggagacag aacatacaga    1860
gcaaaagcga aatgtgattc gaattattcc tcaccacaac tacaatgcag ctattaataa    1920
gtacaaccat gacattgccc ttctggaact ggacgaaccc ttagtgctaa acagctacgt    1980
tacacctatt tgcattgctg acaaggaata cacgaacatc ttcctcaaat ttggatctgg    2040
```

```
ctatgtaagt ggctggggaa gagtcttcca caaagggaga tcagctttag ttcttcagta    2100
ccttagagtt ccacttgttg accgagccac atgtcttcga tctacaaagt tcaccatcta    2160
taacaacatg ttctgtgctg gcttccatga aggaggtaga gattcatgtc aaggagatag    2220
tgggggaccc catgttactg aagtggaagg accagtttc ttaactggaa ttattagctg     2280
gggtgaagag tgtgcaatga aaggcaaata tggaatatat accaaggtgt cccggtatgt    2340
caactggatt aaggaaaaaa caaagctcac tgacaaaact cacacatgcc caccgtgccc    2400
agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520
ccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760
cctgccccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta aatgagaatt    3060
cagacatgat aagatacatt gatgagtttg gacaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat ccccgcgctg gaggatcatc    3240
cagccggcgt cccggaaaac gattccgaag cccaacccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga cagggtcac gtcgtcccgg accacaccgg cgaagtcgtc ctccacgaag    3600
tcccgggaga cccgagccg tcggtccag aactcgaccg ctccggcgac gtcgcgcgcg     3660
gtgagcaccg aacggcact ggtcaacttg gccatggttt agttcctcac cttgtcgtat     3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taaataaaaa    3900
aaattagtca gccatggggc ggagaatggg cggaactggg cggagttagg ggcgggatgg    3960
gcggagttag gggcgggact atggttgctg actaattgag atgcatgctt tgcatacttc    4020
tgcctgctgg ggagcctggg gactttccac acctggttgc tgactaattg agatgcatgc    4080
tttgcatact tctgcctgct ggggagcctg gggactttcc acaccctcgt cgagctagct    4140
tcgtgaggct ccggtgcccg tcagtgggca gagcgcacat cgcccacagt ccccgagaag    4200 ttgggggag gggtcggcaa ttgaaccggt gcctagagaa ggtggcgcgg ggtaaactgg     4260
gaaagtgatg tcgtgtactg gctccgcctt tttcccgagg gtgggggaga accgtatata    4320
agtgcagtag tcgccgtgaa cgttcttttt cgcaacgggt ttgccgccag aacacaggta    4380
```

-continued

```
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
ggccttgcgc tttaggagcc ccttcgcctc gtgcttgagt tgaggcctgg cctgggcgct    4560
ggggccgccg cgtgcgaatc tggtggcacc ttcgcgcctg tctcgctgct ttcgataagt    4620
ctctagccat ttaaaatttt tgatgacctg ctgcgacgct ttttttctgg caagatagtc    4680
ttgtaaatgc gggccaggat ctgcacactg gtatttcggt ttttggggcc gcgggcggcg    4740
acggggcccg tgcgtcccag cgcacatgtt cggcgaggcg gggcctgcga gcgcggccac    4800
cgagaatcgg acggggggtag tctcaagctg gccggcctgc tctggtgcct ggcctcgcgc    4860
cgccgtgtat cgccccgccc tgggcggcaa ggctggcccg gtcggcacca gttgcgtgag    4920
cggaaagatg gccgcttccc ggccctgctc caggggctc aaaatggagg acgcggcgct    4980
cgggagagcg ggcgggtgag tcacccacac aaaggaaagg ggcctttccg tcctcagccg    5040
tcgcttcatg tgactccacg gagtaccggg cgccgtccag gcacctcgat tagttctgga    5100
gcttttggag tacgtcgtct ttaggttggg gggagggggtt ttatgcgatg gagtttcccc    5160
acactgagtg ggtggagact gaagttaggc cagcttggca cttgatgtaa ttctccttgg    5220
aatttgccct ttttgagttt ggatcttggt tcattctcaa gcctcagaca gtggttcaaa    5280
gtttttttct tccatttcag gtgtcgtgaa cacgtggtcg cggccgcgcc gccaccatgg    5340
agacagacac actcctgcta tgggtactgc tgctctgggt tccaggttcc actggtgaca    5400
aaactcacac atgcccaccg tgcccagcac ctgaactcct gggaggaccg tcagtcttcc    5460
tcttcccccc aaaacccaag gacaccctca tgatctcccg gacccctgag gtcacatgcg    5520
tggtggtgga cgtgagccac gaagaccctg aggtcaagtt caactggtac gtggacggcg    5580
tggaggtgca taatgccaag acaaagccgc gggaggagca gtacaacagc acgtaccgtg    5640
tggtcagcgt cctcaccgtc ctgcaccagg actggctgaa tggcaaggag tacaagtgca    5700
aggtctccaa caaagccctc ccagccccca tcgagaaaac catctccaaa gccaagggc    5760
agccccgaga accacaggtg tacaccctgc ccccatcccg cgatgagctg accaagaacc    5820
aggtcagcct gacctgcctg gtcaaaggct tctatcccag cgacatcgcc gtggagtggg    5880
agagcaatgg gcagccggag aacaactaca agaccacgcc tcccgtgttg gactccgacg    5940
gctccttctt cctctacagc aagctcaccg tggacaagag caggtggcag caggggaacg    6000
tcttctcatg ctccgtgatg catgaggctc tgcacaacca ctacacgcag aagagcctct    6060
ccctgtctcc gggtaaatga ctcgagagat ctggccggct gggcccgttt cgaaggtaag    6120
cctatcccta accctctcct cggtctcgat tctacgcgta ccggtcatca tcaccatcac    6180
cattgagttt aaacccgctg atcagcctcg actgtgcctt ctagttgcca gccatctgtt    6240
gtttgcccct cccccgtgcc ttccttgacc ctggaaggtg ccactcccac tgtcctttcc    6300
taataaaatg aggaaattgc atcgcattgt ctgagtaggt gtcattctat tctggggggt    6360
ggggtggggc aggacagcaa gggggaggat tgggaagaca atagcaggca tgctgggat    6420
gcggtgggct ctatggcttc tgaggcggaa agaaccagtg gcggtaatac ggttatccac    6480
agaatcaggg gataacgcag gaaagaacat gtgagcaaaa ggccagcaaa aggccaggaa    6540
ccgtaaaaag gccgcgttgc tggcgttttt ccataggctc cgcccccctg acgagcatca    6600
caaaaatcga cgctcaagtc agaggtggcg aaacccgaca ggactataaa gataccaggc    6660
gtttccccct agaagctccc tcgtgcgctc tcctgttccg accctgccgc ttaccggata    6720
cctgtccgcc tttctccctt cgggaagcgt ggcgctttct catagctcac gctgtaggta    6780
```

```
tctcagttcg gtgtaggtcg ttcgctccaa gctgggctgt gtgcacgaac ccccgttca    6840 gcccgaccgc tgcgccttat ccggtaacta tcgtcttgag tccaacccgg taagacacga    6900
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggg ctggcttaac tatgcggcat cagagcagat    7440
tgtactgaga gtgcaccata tatgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                           7583
```

<210> SEQ ID NO 2
<211> LENGTH: 642
<212> TYPE: PRT
<213> ORGANISM: Artificial Sequence
<220> FEATURE:
<223> OTHER INFORMATION: FIX-Fc Chain

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu

```
            210                 215                 220
Thr Gly Val Lys Ile Thr Val Ala Gly Glu His Asn Ile Glu Glu
225                 230                 235                 240

Thr Glu His Thr Glu Gln Lys Arg Asn Val Ile Arg Ile Ile Pro His
                    245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
            275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
            355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Asp
                405                 410                 415

Lys Thr His Thr Cys Pro Pro Cys Pro Ala Pro Glu Leu Leu Gly Gly
                420                 425                 430

Pro Ser Val Phe Leu Phe Pro Pro Lys Pro Lys Asp Thr Leu Met Ile
            435                 440                 445

Ser Arg Thr Pro Glu Val Thr Cys Val Val Val Asp Val Ser His Glu
450                 455                 460

Asp Pro Glu Val Lys Phe Asn Trp Tyr Val Asp Gly Val Glu Val His
465                 470                 475                 480

Asn Ala Lys Thr Lys Pro Arg Glu Glu Gln Tyr Asn Ser Thr Tyr Arg
                485                 490                 495

Val Val Ser Val Leu Thr Val Leu His Gln Asp Trp Leu Asn Gly Lys
            500                 505                 510

Glu Tyr Lys Cys Lys Val Ser Asn Lys Ala Leu Pro Ala Pro Ile Glu
        515                 520                 525

Lys Thr Ile Ser Lys Ala Lys Gly Gln Pro Arg Glu Pro Gln Val Tyr
        530                 535                 540

Thr Leu Pro Pro Ser Arg Asp Glu Leu Thr Lys Asn Gln Val Ser Leu
545                 550                 555                 560

Thr Cys Leu Val Lys Gly Phe Tyr Pro Ser Asp Ile Ala Val Glu Trp
                565                 570                 575

Glu Ser Asn Gly Gln Pro Glu Asn Asn Tyr Lys Thr Thr Pro Pro Val
            580                 585                 590

Leu Asp Ser Asp Gly Ser Phe Phe Leu Tyr Ser Lys Leu Thr Val Asp
        595                 600                 605

Lys Ser Arg Trp Gln Gln Gly Asn Val Phe Ser Cys Ser Val Met His
        610                 615                 620

Glu Ala Leu His Asn His Tyr Thr Gln Lys Ser Leu Ser Leu Ser Pro
625                 630                 635                 640
```

Gly Lys

<210> SEQ ID NO 3
<211> LENGTH: 741
<212> TYPE: DNA
<213> ORGANISM: Artificial Sequence
<220> FEATURE:
<223> OTHER INFORMATION: Fc Portion

<400> SEQUENCE: 3

```
atggagacag acacactcct gctatgggta ctgctgctct gggttccagg ttccactggt    60
gacaaaactc acacatgccc accgtgccca gcacctgaac tcctgggagg accgtcagtc   120
ttcctcttcc ccccaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc aagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc cccatcgaga aaaccatctc caaagccaaa   420
gggcagcccc gagaaccaca ggtgtacacc ctgcccccat cccgcgatga gctgaccaag   480
aaccaggtca gcctgacctg cctggtcaaa ggcttctatc ccagcgacat cgccgtggag   540
tgggagagca atgggcagcc ggagaacaac tacaagacca cgcctcccgt gttggactcc   600
gacggctcct tcttcctcta cagcaagctc accgtggaca agagcaggtg gcagcagggg   660
aacgtcttct catgctccgt gatgcatgag gctctgcaca accactacac gcagaagagc   720
ctctccctgt ctccgggtaa a                                             741
```

<210> SEQ ID NO 4
<211> LENGTH: 227
<212> TYPE: PRT
<213> ORGANISM: Artificial Sequence
<220> FEATURE:
<223> OTHER INFORMATION: Fc Portion

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

```
                        -continued

Trp Glu Ser Asn Gly Gln Pro Glu Asn Asn Tyr Lys Thr Thr Pro Pro
                165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro Gly Lys
225
```

FACTOR IX POLYPEPTIDE FORMULATIONS

REFERENCE TO SEQUENCE LISTING SUBMITTED ELECTRONICALLY VIA EFS-WEB

The content of the electronically submitted sequence listing (Name: 2159_4140001_SequenceListing.txt; 19,086 bytes; and Date of Creation: Aug. 18, 2015) was originally submitted in the International Application No. PCT/US2014/029010 and is incorporated herein by reference in its entirety.

BACKGROUND

The present invention relates generally to the field of therapeutics for hemostatic disorders.

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual will suffer from spontaneous bleeding in the joints, which produces severe pain and debilitating immobility; bleeding into muscles results in the accumulation of blood in those tissues; spontaneous bleeding in the throat and neck can cause asphyxiation if not immediately treated; renal bleeding; and severe bleeding following surgery, minor accidental injuries, or dental extractions also are prevalent.

Normal in vivo blood coagulation at minimum requires the serine proteases Factors II (prothrombin), VII, IX, X and XI (soluble plasma proteins); cofactors including the transmembrane protein tissue factor and the plasma proteins Factors V and VIII; fibrinogen, the transglutaminase Factor XIII, phospholipid (including activated platelets), and calcium. Additional proteins including kallikrein, high molecular weight kininogen, and Factor XII are required for some in vitro clotting tests, and can play a role in vivo under pathologic conditions.

In hemophilia, blood clotting is disturbed by a lack of certain plasma blood clotting factors. Hemophilia B is caused by a deficiency in Factor IX that can result from either the decreased synthesis of the Factor IX protein or a defective molecule with reduced activity. The treatment of hemophilia occurs by replacement of the missing clotting factor by exogenous factor concentrates highly enriched in Factor IX. However, generating such a concentrate from blood is fraught with technical difficulties, as is described below.

Purification of Factor IX from plasma (plasma derived Factor IX; pdFIX) almost exclusively yields active Factor IX. However, such purification of Factor IX from plasma is very difficult because Factor IX is only present in low concentration in plasma (5 µg/mL. Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant factor IX (rFIX) is also available, but suffers from the same short half-life and need for frequent dosing (e.g., 2-3 times per week for prophylaxis) as pdFIX. rFIX also has a lower incremental recovery (K value) compared to pdFIX, which necessitates the use of higher doses of rFIX than those for pdFIX.

Reduced mortality, prevention of joint damage and improved quality of life have been important achievements due to the development of plasma-derived and recombinant Factor IX. Prolonged protection from bleeding would represent another key advancement in the treatment of hemophilia B subjects. However, to date, no products that allow for prolonged protection have been developed. Therefore, there remains a need for improved methods of treating hemophilia due to Factor IX deficiency that are more tolerable and more effective than current therapies.

BRIEF SUMMARY OF THE INVENTION

The present invention is directed to a pharmaceutical composition comprising: (a) a Factor IX polypeptide comprising human Factor IX fused to an FcRn Binding Partner (rFIXFBP polypeptide), wherein the polypeptide has long-acting Factor IX activity; (b) a carbohydrate mixture comprising sucrose and mannitol; (c) sodium chloride (NaCl); (d) L-histidine; and (e) polysorbate 20 or polysorbate 80. In one embodiment, the pharmaceutical composition comprises about 1% (w/v) to about 2% (w/v) sucrose (e.g., about 1.2% (w/v) or about 1.7% (w/v) sucrose) or about 10 mg/ml to about 20 mg/ml sucrose (e.g., about 11.9 mg/ml or about 16.7 mg/ml sucrose). In another embodiment, the pharmaceutical composition comprises about 2% (w/v) to about 4% (w/v) mannitol (e.g., about 2.4% (w/v) mannitol or about 3.3% (w/v) mannitol) or about 20 mg/ml to about 40 mg/ml mannitol (e.g., about 23.8 mg/ml mannitol or about 33.3 mg/ml mannitol). In other embodiments, the pharmaceutical composition comprises between about 50 mM and about 60 mM NaCl (e.g., about 55.6 mM NaCl) or between about 3 mg/ml and about 4 mg/ml NaCl (e.g., about 3.25 mg/ml NaCl). In some embodiments, the pharmaceutical composition comprises between about 20 mM and about 40 mM L-histidine (e.g., about 25 mM L-histidine or about 35 mM L-histidine) or between about 3 mg/ml and about 6 mg/ml L-histidine (e.g., about 3.88 mg/ml L-histidine or about 5.43 mg/ml L-histidine). In certain embodiments, the pharmaceutical composition comprises between about 0.008% (w/v) and about 0.020% (w/v) polysorbate 20 or polysorbate 80 (e.g., about 0.010% (w/v) polysorbate 20 or polysorbate 80 or about 0.014% (w/v) polysorbate 20 or polysorbate 80) or between about 0.08 mg/ml and about 0.2 mg/ml polysorbate 20 or polysorbate 80 (e.g., about 0.10% mg/ml polysorbate 20 or polysorbate 80 or about 0.14 mg/ml polysorbate 20 or polysorbate 80).

The pharmaceutical composition can comprise an rFIXFBP polypeptide, which is rFIXFc polypeptide comprising a first subunit which comprises an amino acid sequence at least 90% or 95% identical to amino acids 1 to 642 of SEQ ID NO:2, and a second subunit which comprises an amino acid sequence at least 90% to 100% identical to amino acids 1 to 227 of SEQ ID NO:4.

In some aspects, the rFIXFBP polypeptide with Factor IX activity is present at a concentration of between about 25 IU/ml and about 1200 IU/ml (e.g., 50 IU/ml, 100 IU/ml, 200 IU/ml, 400 IU/ml, or 600 IU/ml of the rFIXFBP polypeptide).

In one aspect, a pharmaceutical composition comprises: (a) between about 25 IU/ml and about 700 IU/ml of a rFIXFBP polypeptide; (b) between about 1% (w/v) and about 2% (w/v) of sucrose; (c) between about 2% (w/v) and about 4% (w/v) of mannitol; (d) between about 50 mM and about 60 mM NaCl; (e) between about 20 mM and about 40 mM L-histidine; and (f) between about 0.008% (w/v) and about 0.015% of polysorbate 20 or polysorbate 80. For example, a pharmaceutical composition can comprise: (a) about 50 IU/ml, about 100 IU/ml, about 200 IU/ml, or about 400 IU/ml of a rFIXFBP polypeptide; (b) about 1.2% (w/v) of sucrose; (c) about 2.4% (w/v) of mannitol; (d) about 55.6 mM NaCl; (e) about 25 mM L-histidine; and (f) about 0.010% (w/v) of polysorbate 20 or polysorbate 80.

In another aspect, a pharmaceutical composition comprises: (a) about 600 IU/ml of a rFIXFBP polypeptide; (b) about 1.7% (w/v) of sucrose; (c) about 3.3% (w/v) of mannitol; (d) about 55.6 mM NaCl; (e) about 35 mM L-histidine; and (f) about 0.014% (w/v) of polysorbate 20 or polysorbate 80.

In other aspects, a pharmaceutical composition comprises: (a) between about 25 IU/ml and about 700 IU/ml of a rFIXFBP polypeptide; (b) between about 10 mg/ml and about 20 mg/ml of sucrose; (c) between about 20 mg/ml and about 40 mg/ml of mannitol; (d) between about 3 mg/ml and about 4 mg/ml NaCl; (e) between about 3 mg/ml and about 6 mg/ml L-histidine; and (f) between about 0.08 mg/ml and about 0.15 mg/ml of polysorbate 20 or polysorbate 80. For example, a pharmaceutical composition comprises: (a) about 50 IU/ml, about 100 IU/ml, about 200 IU/ml, or about 400 IU/ml of a rFIXFBP polypeptide; (b) about 11.9 mg/ml of sucrose; (c) about 23.8 mg/ml of mannitol; (d) about 3.25 mg/ml NaCl; (e) about 3.88 mg/ml L-histidine; and (f) about 0.10 mg/ml of polysorbate 20 or polysorbate 80. In some aspects, a pharmaceutical composition comprises: (a) about 600 IU/ml of a rFIXFBP polypeptide; (b) about 16.7 mg/ml of sucrose; (c) about 33.3 mg/ml of mannitol; (d) about 3.25 mg/ml NaCl; (e) about 5.43 mg/ml L-histidine; and (f) about 0.14 mg/ml of polysorbate 20 or polysorbate 80.

In certain aspects, the invention is directed to a pharmaceutical kit comprising: (a) a first container comprising a lyophilized powder, wherein the powder comprises (i) a rFIXFBP polypeptide, (ii) sucrose; (iii) mannitol; (iv) L-histidine; and (v) polysorbate 20 or polysorbate 80; and (b) a second container comprising 0.325% (w/v) NaCl to be combined with the lyophilized powder of the first container. In one embodiment, the pharmaceutical kit comprises: (a) a first container comprising a lyophilized powder, where the powder comprises (i) about 250 IU, about 500 IU, about 1000 IU, or about 2000 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and (b) a second container comprising 0.325% (w/v) NaCl at a volume sufficient to produce, when combined with the lyophilized powder of the first container, a solution comprising: (i) about 50 IU/ml, about 100 IU/ml, about 200 IU/ml, or about 400 IU of a rFIXFBP polypeptide, respectively; (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80. In another embodiment, the pharmaceutical kit comprises: (a) a first container comprising a lyophilized powder, where the powder comprises (i) about 3000 IU of a rFIXFBP polypeptide, (ii) about 83.3 mg of sucrose; (iii) about 167 mg of mannitol; (iv) about 27.2 mg of L-histidine; and (v) about 0.7 mg of polysorbate 20 or polysorbate 80; and (b) a second container comprising 0.325% (w/v) NaCl at a volume sufficient to produce, when combined with the lyophilized powder of the first container, a solution comprising: (i) about 600 IU/ml of a rFIXFBP polypeptide; (ii) about 1.7% (w/v) of sucrose; (iii) about 33% (w/v) of mannitol; (iv) about 55.6 mM NaCl; (v) about 35 mM L-histidine; and (vi) about 0.014% (w/v) of polysorbate 20 or polysorbate 80.

In some aspects, the invention provides a method of administering a rFIXFBP polypeptide to a hemophilia B subject in need of prophylaxis, comprising intravenously administering to the subject a pharmaceutical composition of the invention at an initial dose of about 50 IU/kg, administered once per week or at an initial dose of about 100 IU/kg, administered once every 10 to 14 days, wherein the administration prevents or reduces the frequency of bleeding episodes in the subject. In other aspects, the invention provides a method of administering a rFIXFBP polypeptide to a hemophilia B subject in need of treatment of a minor to moderate bleeding episode, comprising intravenously administering to the subject a pharmaceutical composition of the invention at an initial dose of about 30 IU/kg to about 60 IU/kg, wherein the administration controls, alleviates, or reverses the bleeding episode. The method can further comprise administering one or more additional doses every 48 hours if the subject exhibits further evidence of bleeding. In yet other aspects, the invention includes a method of administering a rFIXFBP polypeptide to a hemophilia B subject in need of treatment of a major bleeding episode, comprising intravenously administering to the subject a pharmaceutical composition of the invention at an initial dose of about 100 IU/kg, wherein the administration controls, alleviates, or reverses the bleeding episode. In one embodiment, the method further comprises administering an additional dose of the pharmaceutical composition at about 80 IU/kg after about 6 to 10 hours if the bleeding episode continues, in another embodiment, the method further comprises administering one or more additional doses of the pharmaceutical composition at 80 IU/kg every 24 hours for three days if the bleeding episode continues. In other embodiment, the method further comprises administering one or more additional doses of the pharmaceutical composition at 80 IU/kg every 48 hours until the bleeding episode is controlled.

In other aspects, the invention includes a method of administering a rFIXFBP polypeptide to a hemophilia B subject in need of surgical prophylaxis, comprising intravenously administering to a hemophila B subject undergoing minor surgery a pharmaceutical composition of the invention at a dose of about 50 IU/kg to 80 IU/kg, wherein the administration controls bleeding in the subject during and after surgery, one embodiment, the method further comprises administering an additional dose of the pharmaceutical composition at about 50 IU/kg to 80 IU/kg at about 24 to about 48 hours after surgery if needed to control post-operative bleeding.

In still other aspects, the invention provides a method of administering a rFIXFBP polypeptide to a hemophilia B subject in need of surgical prophylaxis, comprising intravenously administering to a hemophila B subject undergoing major surgery a pharmaceutical composition of the invention at a dose of about 100 IU/kg, wherein the administration controls bleeding in the subject during and after surgery. In one embodiment, the method further comprises administering an additional dose of the pharmaceutical composition at about 80 IU/kg after about 6 to 10 hours if needed to control post-operative bleeding. In another embodiment, the method further comprises administering one or more additional doses of the pharmaceutical composition at 80 IU/kg every 24 hours for three days if needed to control post-operative bleeding. In other embodiments, the method further comprises administering one or more additional doses of the pharmaceutical composition at 80 IU/kg every 48 hours if needed to control post-operative bleeding.

In yet other aspects, the desired dose of the rFIXFBP polypeptide is obtainable from a single pharmaceutical kit of the invention or from two or more pharmaceutical kits of the invention, and wherein the contents of the two or more pharmaceutical kits are pooled prior to administration.

DETAILED DESCRIPTION

This disclosure provides a method of treating FIX deficiency, e.g., Hemophilia B, by administering a chimeric rFIXFBP polypeptide using optimal formulations, optimal dosing intervals, optimal dosing frequencies, and/or optimal pharmacokinetic parameters. Also provided are formulations and pharmaceutical kits for administration of rFIXFBP.

Definitions

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "polypeptide," "peptide" and "protein" are used interchangeably and refer to a polymeric compound comprised of covalently linked amino acid residues.

The term "polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses.

The term "administering," as used herein, means to, e.g., prescribe or give a pharmaceutical composition comprising a long-acting rFIXFBP polypeptide to a subject. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration. A pharmaceutical composition comprising a long-acting rFIXFBP polypeptide can comprise one or more excipients, as described herein. Advantages of the methods, compositions, and pharmaceutical kits provided herein include: improved regimen compliance; reduced break through bleeds; increased protection of joints from bleeds; prevention of joint damage; reduced morbidity; reduced mortality; prolonged protection from bleeding; decreased thrombotic events; and improved quality of life.

The terms "rFIXFBP" or "rFIXFBP polypeptide," as used herein refer to a recombinant fusion protein comprising human coagulation Factor IX (FIX) and an FcRn Binding Partner (rFIXFBP). FcRn binding partner ("FBP") comprises functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An FcRn BP can comprise the CH2 and CH3 domains of an immunoglobulin with or without the hinge region of the immunoglobulin. Exemplary FcRn BP variants are provided in WO 2004/101740 and WO 2006/074199, incorporated herein by reference in its entirety.

In one embodiment, rFIXBP is rFIXFc, a recombinant fusion protein comprised of human coagulation Factor IX (FIX) and an Fc domain of a human antibody (IgG1 isotype). See, e.g., PCT Application No. PCT/US2011/043569, filed Jul. 11, 2011 and published as WO 2012/006624, which is incorporated herein by reference in its entirety. The rFIXFc polypeptide is a heterodimeric protein with a FIXFc single chain (FIXFc-sc) and an Fc single chain (Fc-sc) bound together through two disulfide bonds in the hinge region of Fc. rFIXFc requires two protein subunits, FIXFc-sc (642 amino acids, SEQ ID NO:2) and Fc-sc (227 amino acids, SEQ ID NO:4), to assemble within a transfected cell line to form the final protein product, rFIXFc. The polynucleotide sequences encoding FIXFc-sc and Fc-sc are presented as SEQ ID NO:1 and SEQ ID NO:3, respectively.

The Factor IX portion of rFIXFc has a primary amino acid sequence that is identical to the Thr148 allelic form of plasma derived Factor IX and has structural and functional characteristics similar to endogenous Factor IX. The Fc domain of rFIXFc contains the hinge, CH2 and CH3 regions of IgG1. The assembled heterodimer mature form of rFIXFc contains 869 amino acids with a molecular weight of approximately 98 kilodaltons.

rFIXBP is produced by recombinant DNA technology in a human embryonic kidney (HEK) cell line. The cell line expresses rFIXFBP into a defined cell culture medium that does not contain any proteins derived from animal or human sources. rFIXFBP is purified by a series of chromatography steps that does not require use of a monoclonal antibody. The process includes multiple viral clearance steps including 15 nm virus-retaining nano-filtration. No human or animal additives are used in the cell culture, purification, and formulation processes.

The terms "long-acting" and "long-lasting" are used interchangeably herein. In one embodiment, the term "long-acting" or "long-lasting" indicates that a FIX activity as a result of administration of the rFIXFBP polypeptide is longer than the FIX activity of a wild-type FIX (e.g., BENEFIX® or plasma-derived FIX ("pdFIX")). The "longer" FIX activity can be measured by any known methods in the art, e.g., aPTT assay, chromogenic assay, ROTEM, TGA, and etc. In one embodiment, the "longer" FIX activity can be shown by the $T_{1/2beta}$ (activity). In another embodiment, the "longer" FIX activity can be inferred by the level of FIX antigen present in plasma, e.g., by the $T_{1/2beta}$ (antigen).

Factor IX coagulant activity is expresses as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

The term "lyophilizate" or "lyophilisate" as used herein in connection with the formulation according to the invention denotes a formulation which is manufactured by freeze-drying methods known in the art per se. The solvent (e.g. water) is removed by freezing following sublimation under vacuum and desorption of residual water at elevated temperature. In the pharmaceutical field, the lyophilizate has usually a residual moisture of about 0.1 to 5% (w/w) and is present as a powder or a physical stable cake. The lyophilizate is characterized by a fast dissolution after addition of a reconstitution medium.

The term "reconstituted formulation" as used herein denotes a formulation which is lyophilized and re-dissolved by addition of a diluent. The diluent can contain, without limitation, water for injection (WFI), bacteriostatic water for injection (BWFI), sodium chloride solutions (e.g. 0.9% (w/v) NaCl), glucose solutions (e.g. 5% glucose), surfactant containing solutions (e.g. 0.01% polysorbate 20 or polysorbate 80), a pH-buffered solution (e.g. phosphate-buffered solutions) and combinations thereof.

"Dosing interval," as used herein, means the amount of time that elapses between multiple doses being administered to a subject. Dosing interval can thus be indicated as ranges. The dosing interval for a rFIXFBP polypeptide in the methods provided herein can be at least about one and one-half to eight times longer than the dosing interval required for an equivalent amount (in IU/kg) of wild-type Factor IX.

The term "dosing frequency" as used herein refers to the frequency of administering doses of a rFIXFBP polypeptide in a given time. Dosing frequency can be indicated as the number of doses per a given time, e.g., once a week or once in two weeks.

The terms "prophylaxis of one or more bleeding episodes" or "prophylactic treatment" as used herein mean administering a rFIXFBP polypeptide in regular, multiple doses to a subject over a course of time to increase the level of Factor IX activity in a subject's plasma, thereby preventing bleeding episodes from occurring. In one embodiment, "prophylaxis of one or more bleeding episodes" indicates use of a rFIXFBP polypeptide to prevent or inhibit occurrence of one or more spontaneous or uncontrollable bleeding or bleeding episodes or to reduce the frequency of one or more spontaneous or uncontrollable bleeding or bleeding episodes. In another embodiment, the increased FIX activity level is sufficient to decrease the incidence of spontaneous bleeding or to prevent bleeding in the event of an unforeseen injury. Prophylactic treatment decreases or prevents bleeding episodes, for example, those described under on-demand treatment. Prophylactic treatment can be individualized, as discussed under "dosing interval", e.g., to compensate for inter-subject variability.

The term "about once a week" as used herein is meant to be approximate, and can include every seven days±two days, i.e., every five days to every nine days. The dosing frequency of "about once a week" thus can be every five days, every six days, every seven days, every eight days, or every nine days.

The terms "individualized interval prophylaxis" or "individual prophylaxis," or "tailored prophylaxis" as used herein mean use of a rFIXFBP polypeptide for an individualized dosing interval or frequency to prevent or inhibit occurrence of one or more spontaneous and/or uncontrollable bleeding or bleeding episodes or to reduce the frequency of one or more spontaneous and/or uncontrollable bleeding or bleeding episodes. In one embodiment, the "individualized interval" includes every 10 days±3 days, i.e. every seven days to every 13 days. The dosing frequency of the "individualized interval prophylaxis" thus can be every seven days, every eight days, every nine days, every ten days, every 11 days, every 12 days, or every 13 days.

The term "on-demand treatment," as used herein, means treatment that is intended to take place over a short course of time and is in response to an existing condition, such as a bleeding episode, or a perceived short term need such as planned surgery. The "on-demand treatment" is used interchangeably with "episodic" treatment. Conditions that can require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject can be in need of surgical prophylaxis, peri-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included.

Additional conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

The term "treatment" or "treating" as used herein means amelioration or reduction of one or more symptoms of bleeding diseases or disorders including, but not limited to, hemophilia B. In one embodiment, "treatment of" or "treating" a bleeding disease or disorder includes prevention of one or more symptoms of a bleeding disease or disorder. In a bleeding disease or disorder caused by a FIX deficiency (e.g., a low baseline FIX activity), the term "treatment" or "treating" can mean FIX replacement therapy. By administering a FIXFc polypeptide to a subject, the subject can achieve and/or maintain a plasma trough level of a FIX activity at about 1 IU/dl or above 1 IU/dl. In other embodiments, "treatment" or "treating" means reduction of the frequency of one or more symptoms of bleeding diseases or disorders, e.g., spontaneous or uncontrollable bleeding episodes. "Treatment," however, need not be a cure.

The term "perioperative management" as used herein means use of a FIXFc polypeptide before, concurrently with, or after an operative procedure, e.g., a surgical operation. The use for "perioperative management" of one or more bleeding episode includes surgical prophylaxis before (i.e., preoperative), during (i.e., intraoperative), or after (i.e., postoperative) a surgery to prevent one or more bleeding or bleeding episode or reducing or inhibiting spontaneous and/or uncontrollable bleeding episodes before, during, and after a surgery.

Pharmacokinetic (PK) parameters include the terms above and the following terms, which have their ordinary meaning in the art, unless otherwise indicated. Some of the terms are explained in more detail in the Examples. PK parameters can be based on FIX antigen level (often denoted parenthetically herein as "antigen") or FIX activity level (often denoted parenthetically herein as "activity"). In the literature, PK parameters are often based on FIX activity level due to the presence in the plasma of some subjects of endogenous, inactive FIX, which interferes with the ability to measure administered exogenous) FIX using antibody against FIX. However, when FIX is administered as part of an Fc fusion protein as provided herein, administered (i.e., exogenous) FIX antigen can be accurately measured using antibody to the heterologous polypeptide. In addition, certain PK parameters can be based on model predicted data (often denoted parenthetically herein as "model predicted") or on observed data (often denoted parenthetically herein as "observed"), and preferably are based on observed data.

"Baseline," as used herein, is the lowest measured plasma Factor level in a subject prior to administering a dose. The Factor IX plasma levels can be measured at two time points prior to dosing: at a screening visit and immediately prior to dosing. Alternatively, (a) the baseline in subjects whose pretreatment FIX activity is <1%, who have no detectable FIX antigen, and have nonsense genotypes can be defined as 0%, (b) the baseline for subjects with pretreatment FIX activity <1% and who have detectable FIX antigen can be set at 0.5%, (c) the baseline for subjects whose pretreatment FIX activity is between 1-2% is Cmin (the lowest activity throughout the PK study), and (d) the baseline for subjects whose pretreatment FIX activity is ≥2% can be set at 2%. Activity above the baseline pre-dosing can be considered residue drug from prior treatment, and can be decayed to baseline and subtracted from the PK data following rFIXFBP dosing.

"$T_{1/2\beta}$," or "$T_{1/2\ beta}$" or "Beta HL," as used herein, is half-life associated with elimination phase, $t_{1/2\beta}=(\ln 2)$/elimination rate constant associated with the terminal phase. The $T_{1/2\ beta}$ can be measured by FIX activity or by FIX antigen level in plasma. The $T_{1/2}$ beta based on activity is shown as $T_{1/2\ beta}$ (activity), and the $T_{1/2\ beta}$ based on the FIX antigen level can be shown as $T_{1/2\ beta}$ (antigen). Both $T_{1/2\ beta}$ (activity) and $T_{1/2\ beta}$ (antigen) can be shown as ranges or a geometric mean.

"Trough," as used herein, is the lowest plasma Factor IX activity level reached after administering a dose of chimeric polypeptide of the invention or another Factor IX molecule and before the next dose is administered, if any. Trough is used interchangeably herein with "threshold." Baseline Factor IX levels are subtracted from measured Factor IX levels to calculate the trough level.

The term "annualized bleeding rate" ("ABR") as used herein refers to the number of bleeding episodes (including spontaneous and traumatic bleeds) experienced by a subject during a defined time period, extrapolated to 1 year. For example two bleeds in six months would indicate an ABR of four. The median. ABR provides a single number to describe all subjects, indicating that half of the subjects had individual ABRs less than or equal to the median and half had ABRs greater than or equal to the median.

"Subject," as used herein means a human. Subject as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia B, who are susceptible to uncontrolled bleeding episodes, e.g., hemophilia, or any combinations thereof. Subjects can also include an individual who is in danger of one or more uncontrollable bleeding episodes prior to a certain activity, e.g., a surgery, a sport activity, or any strenuous activities. The subject can have a baseline FIX activity less than 1.%, less than 0.5%, less than 2%, less than 2.5%, less than 3%, or less than 4%. Subjects also include pediatric humans. Pediatric human subjects are birth to 20 years, preferably birth to 18 years, birth to 16 years, birth to 15 years, birth to 12 years, birth to 11 years, birth to 6 years, birth to 5 years, birth to 2 years, and 2 to 11 years of age.

"Therapeutic dose," "dose," "effective dose," or "dosing amount" as used (interchangeably) herein, means a dose that achieves a plasma trough level of a FIX activity at least about 1 IU/dl or above 1 IU/dl in the subject administered with the FIXFc polypeptide. In one embodiment, the "dose" refers to the amount of the doses that a plasma trough level of a FIX activity is maintained at least about 1 IU/dl or above 1 IU/dl, at least about 2 IU/dl or above 2 IU/dl, at least about 3 IU/dl or above 3 IU/dl, at least about 4 IU/dl or above 4 IU/dl, or at least about 5 IU/dl or above 5 IU/dl throughout the administration of the FIXFc polypeptide. In another embodiment, an "effective dose" reduces or decreases frequency of bleeding or bleeding disorder. In other embodiments, an "effective dose" stops on-going, uncontrollable bleeding or bleeding episodes. In still other embodiments, an "effective dose" prevents spontaneous bleeding or bleeding episodes in a subject susceptible to such spontaneous bleeding or bleeding episodes. A "therapeutic dose" need not cure hemophilia. Exemplary therapeutic doses of an rFIXFBP polypeptide in various bleeding situations are provided herein.

Factor IX-Fc Formulations

This disclosure provides formulations, or pharmaceutical compositions, comprising rFIXFBP. In certain formulations provided herein, rFIXFBP is formulated as a sterile, preservative-free, non-pyrogenic, lyophilized, white to off-white powder to cake, for intravenous (IV) administration. The formulation can be provided in a single-use vial. Certain exemplary formulations of rFIXFBP are also referred to as eftrenonacog alfa.

In certain embodiments, a rFIXFBP formulation is provided in a single-use vial manufactured to contain, following reconstitution with an appropriate amount of diluent, about 50 IU/ml, about 100 IU/ml, about 200 IU/ml, about 400 IU/ml, or about 600 IU/ml rFIXFBP. In certain embodiments in which diluent is added to a final volume of about 5 ml, a single-use vial can nominally contain about 250, about 500, about 1000, about 2000, or about 3000 International Units (IU) of rFIXFBP.

In certain embodiments, rFIXFBP is rFIXFc. In some embodiments, rFIXFc polypeptide comprises an amino acid sequence at least 90%, 95%, or 100% identical to amino acids 1 to 642 of SEQ ID NO:2.

In certain embodiments the formulation includes, in addition to the active rFIXFBP: sucrose (which can act as a stabilizer or bulking agent), mannitol (which can act as a stabilizer or bulking agent), L-histidine (which can act as a buffer), and polysorbate 20 or polysorbate 80 (which can act as a stabilizer). The formulation is provided with a diluent comprising a sterile sodium chloride solution. In certain embodiments, the diluent is provided in a pre-filled syringe.

Accordingly, provided herein is a pharmaceutical composition comprising a specified amount of rFIXFBP (in IU), along with the excipients sucrose, mannitol, L-histidine, NaCl, and polysorbate 20 or polysorbate 80. The compositions provided herein comprise various concentrations of the various excipients, and the concentrations can be expressed in various ways. For example, the concentration of a given excipient can be expressed as a molar concentration (e.g., M or mM) as a weight/volume percent, e.g., grams per 100 ml diluent), or as milligrams per milliliter (mg/ml). Formulations provided herein can contain specified amounts of the various excipients at a level of precision ranging from approximate, e.g., concentrations expressed only to one significant figure (e.g., about 0.1% (w/v)), or with more precision, e.g., out to 2, 3, 4, 5, or 6 significant figures (e.g., about 3.88 mg/ml, with precision out to three significant figures). The necessary level of precision can vary depending on, e.g., the requirements of a given regulatory agency, or the manufacturing process. In certain embodiments the pharmaceutical composition comprises a reconstituted formulation, which can be provided as a lyophilizate, optionally accompanied by a diluent.

In certain embodiments, the pharmaceutical composition comprises about 25 IU/ml to about 1200 IU/ml rFIXFBP, e.g., 50 IU/ml, 100 IU/ml, 200 IU/ml, 400 IU/ml, or 600 IU/ml of rFIXFBP. In certain embodiments, the pharmaceutical composition comprises 50 IU/ml, 100 IU/ml, 200 IU/ml, or 400 IU/ml of rFIXFBP in a formulation comprising about 3.88 mg/ml or about 25 mM L-histidine, about 23.8 mg/ml or about 2.4% (w/v) mannitol, about 11.9 mg/ml or about 1.2% (w/v) sucrose, about 0.10 mg/ml or about 0.010% (w/v) polysorbate 20 or polysorbate 80, and about 3.25 mg/ml or about 55.6 mM NaCl.

In certain embodiments, the pharmaceutical composition comprises 600 IU/ml of rFIXFBP in a formulation comprising about 5.43 mg/ml or about 35 mM L-histidine, about 33.3 mg/ml or about 3.3% (w/v) mannitol, about 16.7 mg/ml or about 1.7% (w/v) sucrose, about 0.14 mg/ml or about 0.014% (w/v) polysorbate 20 or polysorbate 80, and about 3.25 mg/ml or about 55.6 mM NaCl.

In certain embodiments, the pharmaceutical composition comprises a pharmaceutically acceptable amount of sucrose. In certain embodiments, the pharmaceutical composition comprises about 1% (w/v) to about 2% (w/v) sucrose, e.g., about 1.2% (w/v) sucrose or about 1.7% (w/v) sucrose. In certain related embodiments the pharmaceutical composition comprises about 10 mg/ml to about 20 mg/ml sucrose, e.g., about 11.9 mg/ml sucrose or about 16.7 mg/ml sucrose.

In certain embodiments, the pharmaceutical composition comprises a pharmaceutically acceptable amount of mannitol. In certain embodiments, the pharmaceutical composition comprises about 2% (w/v) to about 4% (w/v) mannitol, e.g., about 2.4% (w/v) mannitol or about 3.3% (w/v) mannitol. In certain related embodiments the pharmaceutical composition comprises about 20 mg/ml to about 40 mg/ml mannitol, e.g., about 23.8 mg/ml mannitol or about 33.3 mg/ml mannitol.

In certain embodiments, the pharmaceutical composition comprises pharmaceutically acceptable amounts of both sucrose and mannitol. In certain embodiments, the pharmaceutical composition comprises about 1.0% to about 2.0% sucrose and about 2.0% (w/v) to about 4.0% (w/v) mannitol, e.g., about 1.2% (w/v) sucrose and about 2.4% (w/v) mannitol or about 1.7% (w/v) sucrose and about 3.3% (w/v) mannitol. In certain related embodiments the pharmaceutical composition comprises about 10 mg/ml to about 20 mg/ml sucrose and about 20 mg/ml to about 40 mg/ml mannitol, e.g., about 11.9 mg/ml sucrose and about 23.8 mg/ml mannitol or about 16.7 mg/ml sucrose and about 33.3 mg/ml mannitol. In certain embodiments, sucrose and mannitol are provided as part of a lyophilizate, which, upon reconstitution with an appropriate amount of diluent provides sucrose and mannitol at the desired concentration.

In certain embodiments, the pharmaceutical composition comprises between about 50 mM and about 60 mM NaCl, e.g., about 55.6 mM NaCl. In certain related embodiments, the pharmaceutical composition comprises between about 3 mg/ml and about 4 mg/ml NaCl, e.g., about 3.25 mg/ml NaCl. In certain embodiments, NaCl is provided at the desired concentration in a diluent solution in which a lyophilizate comprising rFIXFBP is reconstituted.

In certain embodiments, the pharmaceutical composition comprises a pharmaceutically acceptable amount of L-histidine. In certain embodiments, the pharmaceutical composition comprises between about 20 mM and about 40 mM L-histidine, e.g., about 25 mM L-histidine or about 35 mM L-histidine. In certain related embodiments the pharmaceutical composition comprises between about 3 mg/ml and about 6 mg/ml L-histidine, e.g., about 3.88 mg/ml L-histidine or about 5.43 mg/ml L-histidine. In certain embodiments, L-histidine is provided as part of a lyophilizate, which, upon reconstitution with an appropriate amount of diluent provides L-histidine at the desired concentration.

In certain embodiments, the pharmaceutical composition comprises a pharmaceutically acceptable amount of polysorbate 20 or polysorbate 80. In certain related embodiments the pharmaceutical composition comprises between about 0.008% (w/v) and about 0.020% (w/v) polysorbate 20 or polysorbate 80, e.g., about 0.010% (w/v) polysorbate 20 or polysorbate 80 or about 0.014% (w/v) polysorbate 20 or polysorbate 80. In certain related embodiments the pharmaceutical composition comprises between about 0.08 mg/ml and about 0.2 mg/ml polysorbate 20 or polysorbate 80, e.g., about 0.10% mg/ml polysorbate 20 or polysorbate 80 or about 0.14 mg/ml polysorbate 20 or polysorbate 80. In certain embodiments, polysorbate 20 or polysorbate 80 is provided as part of a lyophilizate, which, upon reconstitution with an appropriate amount of diluent provides polysorbate 20 or polysorbate 80 at the desired concentration.

In certain embodiments, the pharmaceutical composition comprises: between about 25 IU/ml and about 700 IU/ml of a rFIXFBP polypeptide; between about 1% (w/v) and about 2% (w/v) of sucrose; between about 2% (w/v) and about 4% (w/v) of mannitol; between about 50 mM and about 60 mM NaCl; between about 20 mM and about 40 mM L-histidine; and between about 0.008% (w/v) and about 0.015% of polysorbate 20 or polysorbate 80. In certain embodiments the pharmaceutical composition is provided as a lyophilizate and a diluent. In certain embodiments the amount of lyophilzate provides about 5 ml of a pharmaceutical composition with the desired ingredients at the desired concentrations.

In certain embodiments, the pharmaceutical composition comprises: between about 25 IU/ml and about 700 IU/ml of a rFIXFBP polypeptide; between about 10 mg/ml and about 20 mg/ml of sucrose; between about 20 mg/ml and about 40 mg/ml of mannitol; between about 3 mg/ml and about 4 mg/ml NaCl; between about 3 mg/ml and about 6 mg/ml L-histidine; and between about 0.08 mg/ml and about 0.15 mg/ml of polysorbate 20 or polysorbate 80. In certain embodiments the pharmaceutical composition is provided as a lyophilizate and a diluent. In certain embodiments the amount of lyophilzate provides about 5 ml of a pharmaceutical composition with the desired ingredients at the desired concentrations.

Exemplary compositions are provided in Table 1 and in Table 2 in the Examples.

For example, the disclosure provides a pharmaceutical composition comprising: about 50 IU/ml of a rFIXFBP polypeptide; about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 100 IU/ml of a rFIXFBP polypeptide; about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 200 IU/ml of a rFIXFBP polypeptide; about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 400 IU/ml of a rFIXFBP polypeptide; about 1.2% (w/v) of sucrose; about 2.4% (w/v) of mannitol; about 55.6 mM NaCl; about 25 mM L-histidine; and about 0.010% (w/v) of polysorbate 20 or polysorbate 80. The disclosure further provides a pharmaceutical composition comprising: about 600 IU/ml of a rFIXFBP polypeptide; about 1.7% (w/v) of sucrose; about 3.3% (w/v) of mannitol; about 55.6 mM NaCl; about 35 mM L-histidine; and about 0.014% (w/v) of polysorbate 20 or polysorbate 80.

The disclosure further provides a pharmaceutical composition comprising: about 50 IU/ml of a rFIXFBP polypeptide; about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 100 IU/ml of a rFIXFBP polypeptide; about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 200 IU/ml of a rFIXFBP polypeptide; about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 400 IU/ml of a rFIXFBP polypeptide; about 11.9 mg/ml of sucrose; about 23.8 mg/ml of mannitol; about 3.25 mg/ml NaCl; about 3.88 mg/ml L-histidine; and about 0.10 mg/ml of polysorbate 20 or polysorbate 80. The disclosure further provides a pharmaceutical composition comprising: about 600 IU/ml of a rFIXFBP polypeptide; about 16.7 mg/ml of sucrose; about 33.3 mg/ml of mannitol; about 3.25 mg/ml NaCl; about 5.43 mg/ml L-histidine; and about 0.14 mg/ml of polysorbate 20 or polysorbate 80.

This disclosure also provides the components of a pharmaceutical kit. Such a kit includes one or more containers and optional attachments. A kit as provided herein facilitates administration of an effective amount of rFIXFBP to a subject in need thereof. In certain embodiments, the kit facilitates administration of rFIXFBP via intravenous infusion. In certain embodiments, the kit facilitates self-administration of rFIXFBP via intravenous infusion.

In certain embodiments, the disclosure provides a pharmaceutical kit comprising: a first container comprising a lyophilized powder or cake, where the powder or cake comprises: (i) a rFIXFBP polypeptide, (ii) sucrose; (iii) mannitol; (iv) L-histidine; and (v) polysorbate 20 or polysorbate 80; and a second container comprising a 0.325% (w/v) NaCl diluent solution to be combined with the lyophilized powder of the first container. In certain embodiments, sufficient diluent is provided to produce about 5 ml of a rFIXFBP formulation with desired properties as disclosed herein. In certain embodiments, the second container is a pre-filled syringe associated with a plunger, to allow addition of the diluent to the first container, reconstitution of the contents of the first container, and transfer back into the syringe. In certain embodiments, the kit further provides an adaptor for attaching the syringe to the first container. In certain embodiments the kit further provides a needle and infusion tubing, to be attached to the syringe containing the reconstituted rFIXFBP formulation to allow IV infusion of the formulation.

In certain embodiments rFIXFBP is provided in a total amount from about 200 IU to about 4000 IU, e.g., about 250 IU, about 500 IU, about 1000 IU, about 2000 IU, or about 3000 IU.

In one embodiment, a pharmaceutical kit is provided which comprises a first container comprising a lyophilized powder, where the powder comprises (i) about 250 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80;

and a second container comprising 0.325% (w/v) NaCl at a volume sufficient to produce, when combined with the lyophilized powder of the first container, a solution comprising: (i) about 50 IU/ml of a rFIXFBP polypeptide; (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 500 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 100 IU/ml of a rFIXFBP polypeptide; (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 1000 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 200 IU/ml of a rFIXFBP polypeptide; (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 2000 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 400 IU/ml of a rFIXFBP polypeptide; (ii) about 1.2% (w/v) of sucrose; (iii) about 2.4% (w/v) of mannitol; (iv) about 55.6 mM NaCl; (v) about 25 mM L-histidine; and (vi) about 0.01% (w/v) of polysorbate 20 or polysorbate 80.

In a further embodiment, a pharmaceutical kit is provided which comprises a first container comprising a lyophilized powder, where the powder comprises: (i) about 3000 IU of a rFIXFBP polypeptide, (ii) about 83.3 mg of sucrose; (iii) about 167 mg of mannitol; (iv) about 27.2 mg of L-histidine; and (v) about 0.7 mg of polysorbate 20 or polysorbate 80; and a second container comprising 0.325% (w/v) NaCl at a volume sufficient to produce, when combined with the lyophilized powder of the first container, a solution comprising: (i) about 600 IU/ml of a rFIXFBP polypeptide; (ii) about 1.7% (w/v) of sucrose; (iii) about 3.3% (w/v) of mannitol; (iv) about 55.6 mM NaCl; (v) about 35 mM L-histidine; and (vi) about 0.014% (w/v) of polysorbate 20 or polysorbate 80.

In a further embodiment, a pharmaceutical kit is provided which comprises a first container comprising a lyophilized powder, where the powder comprises: (i) about 250 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 50 IU/ml of a rFIXFBP polypeptide; (ii) about 11.9 mg/ml of sucrose; (iii) about 23.8 mg/ml of mannitol; (iv) about 3.25 mg/ml NaCl; (v) about 3.88 mt·ml L-histidine, and (vi) about 0.10 mg/ml of polysorbate 20 or polysorbate 80.

In a further embodiment, a pharmaceutical kit is provided which comprises a first container comprising a lyophilized powder, where the powder comprises: (i) about 500 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 100 IU/ml of a rFIXFBP polypeptide; (ii) about 11.9 mg/ml of sucrose; (iii) about 23.8 mg/ml of mannitol; (iv) about 3.25 mg/ml NaCl; (v) about 3.88 mg/ml L-histidine; and (vi) about 0.10 mg/ml of polysorbate 20 or polysorbate 80.

In a further embodiment, a pharmaceutical kit is provided which comprises a first container comprising a lyophilized powder, where the powder comprises: (i) about 1000 IU of a rFIXFBP polypeptide, (ii) about 59.5 mg of sucrose; (iii) about 119 mg of mannitol; (iv) about 1.9.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 200 IU/ml of a rFIXFBP polypeptide; (ii) about 11.9 mg/ml of sucrose; (iii) about 23.8 mg/ml of mannitol; (iv) about 125 mg/ml NaCl; (v) about 3.88 mg/ml. L-histidine; and (vi) about 0.10 mg/ml of polysorbate 20 or polysorbate 80.

In a further embodiment, a pharmaceutical kit is provided which comprises a first container comprising a lyophilized powder, where the powder comprises: (i) about 2000 IU of a rFIXFBP polypeptide, (ii) about 59.5 mg of sucrose; (iii) about 119 mg of mannitol; (iv) about 19.4 mg of L-histidine; and (v) about 0.50 mg of polysorbate 20 or polysorbate 80; and a second container comprising 0.325% (w/v) NaCl at a volume sufficient to produce, when combined with the lyophilized powder of the first container, a solution comprising: (i) about 400 of a rFIXFBP polypeptide; (ii) about 11.9 mg/ml of sucrose; (iii) about 23.8 mg/ml of mannitol; (iv) about 3.25 mg/ml NaCl; (v) about 3.88 mg/ml L-histidine; and (vi) about 0.10 nag/nil of polysorbate 20 or polysorbate 80.

In a further embodiment, a pharmaceutical kit is provided which comprises a first container comprising a lyophilized powder, where the powder comprises: (i) about 3000 IU of a rFIXFBP polypeptide, (ii) about 83.3 mg of sucrose; (iii) about 167 mg of mannitol; (iv) about 27.2 mg of L-histidine; and (v) about 0.7 mg of polysorbate 20 or polysorbate 80; and a second container comprising 0.325% (w/v) NaCl at a volume sufficient to produce, when combined with the lyophilized powder of the first container, a solution comprising: (i) about 600 IU/ml of a rFIXFBP polypeptide; (ii) about 16.7 mg/ml of sucrose; (iii) about 33.3 mg/ml of mannitol; (iv) about 3.25 mg/ml NaCl; (v) about 5.43 mg/ml L-histidine; and (vi) about 0.14 mg/ml of polysorbate 20 or polysorbate 80.

In certain embodiments the first container of a pharmaceutical kit provided herein is a glass vial comprising a rubber stopper. In certain embodiments, the second container a pharmaceutical kit provided herein is a syringe body, associated with a plunger. In certain embodiments, the syringe is a pre-filled syringe containing the diluent. In certain embodiments, a pharmaceutical kit provided herein further comprises an adaptor to connect the glass vial to the syringe body. In certain embodiments a pharmaceutical kit provided herein further comprises infusion tubing associated with a needle to be connected to the syringe, suitable for intravenous infusion.

In certain embodiments, a desired dose of rFIXFBP can be achieved through the use of one pharmaceutical kit as provided herein. In certain embodiments, more than one pharmaceutical kit can be used to achieve a desired dose. Provided herein is a method of combining, or pooling the formulations contained in two or more pharmaceutical kits as provided herein in order to achieve a desired dose.

Methods of Administering

The present invention provides methods of administering a 1 rFIXFBP polypeptide to a human subject in need thereof, comprising administering to the subject a specified or calculated dose of a rFIXFBP polypeptide at a specified or calculated dosing interval. Administration of the rFIXFBP polypeptide is a replacement therapy by adding a recombinant FIX to a subject with FIX deficiency. Administration of the rFIXFBP polypeptide can reduce or prevent a number of bleeding or bleeding episodes in the subject.

rFIXFBP is long-acting anti-hemophilic factor (recombinant) indicated in adults and children (≥12 years) with hemophilia B (congenital Factor IX deficiency) for, e.g., control and prevention of bleeding episodes, routine prophylaxis to prevent or reduce the frequency of bleeding episodes, and perioperative management (surgical prophylaxis).

A subject as used herein is a human subject in need of control or prevention of bleeding or bleeding episodes. The subject can be bleeding at the time of administration or be expected to be bleeding, or can be susceptible to bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those in need of peri-operative management, such as management of bleeding associated with surgery or dental extraction. In one embodiment, the subject is in need of prophylaxis of one or more bleeding episodes. In another embodiment, the subject is in need of individualized interval prophylaxis. In other embodiments, the subject is in need of on-demand treatment of one or more bleeding episodes. In still other embodiments, the subject is in need of perioperative management of one or more bleeding episodes.

Provided herein are optimized and/or appropriate dosing amounts and dosing intervals for use with the formulations, pharmaceutical compositions, and/or one or more pharmaceutical kits provided herein that can treat or prevent one or more bleeding episodes. Administration of the appropriate dosing amount for the dosing interval can achieve a plasma trough level of a FIX activity at least about 1 IU/dl or above 1 IU/dl during the interval in a subject administered with a rFIXFBP polypeptide. In one embodiment, the invention includes a dosing amount (or ranges of the dosing amount) and a dosing interval (or ranges of the dosing interval) that can maintain a plasma trough level of a FIX activity at least about 1 IU/dl (1%) or above 1 IU/dl (1%), at least about 2 IU/dl (2%) or above 2 IU/dl (2%), at least about 3 IU/dl (3%) or above 3 IU/dl (3%), at least about 4 IU/dl (4%) or above 4 IU/dl (4%), or at least about 5 IU/dl (5%) or above 5 IU/dl (5%) throughout the interval. In another embodiment, a dosing amount (or ranges of the dosing amount) and a dosing interval (or ranges of the dosing interval) that reduces or decreases frequency of bleeding or bleeding disorder.

In certain embodiments, the desired trough level of FIX activity is achieved through prophylactic treatment of rFIXFBP by a fixed dose at a fixed interval, a fixed dose at an individualized interval, an individualized dose at a fixed interval, or an individualized dose at an individualized interval.

In certain embodiments, the desired trough level of FIX activity is achieved through prophylactic administration of a fixed amount of rFIXFBP at a fixed interval. For example, rFIXFBP can be administered in an amount of about 50 IU/kg at an interval of about one week (e.g., every seven days), or rFIXFBP can be administered in an amount of about 100 IU/kg at an interval of about 10 days to about 14 days. In certain embodiments the subject's trough levels of FIX activity can be measured during a fixed dose and fixed interval schedule, and the dose and/or interval can be adjusted to achieve a desired trough level. In certain embodiments the average individualized weekly dose in a group of hemophilia B subjects is between about 30 IU/Kg and about 60 IU/kg, e.g., about 32 IU/kg and about 54 IU/kg, e.g., 32, 33, 34, 35, 36, 37, 38, 39, 40, 41, 42, 43, 44, 45, 56, 47, 48, 49, 50, 51, 52, 53, or 54 IU/kg, e.g., about 41 IU/kg. In certain embodiments the average individuals dosing interval for administration of 100 IU/kg is between about 10 days and about 14 days, e.g., 10 days, 11 days, 12 days, 13 days, or 14 days, e.g., about 13 days.

In certain embodiments, prophylactic administration of rFIXFBP can reduce the subject's annualized bleeding rate (ABR) by at least 70% over the average annualized bleeding rate in subjects treated by an episodic (on demand) protocol.

In certain embodiments where a hemophilia B subject is treated prophylactically via a fixed dose at a fixed interval, e.g., 50 IU/kg once weekly or 100 IU/kg once every 10 days, 11 days, 12 days, 13 days, or 14 days.

In certain embodiments where a hemophilia B subject is treated prophylactically via an individualized dose at a fixed interval, e.g., e.g., between about 30 IU/Kg and about 60 IU/kg once weekly, e.g., about 32 IU/kg and about 54 IU/kg once weekly, e.g., 32, 33, 34, 35, 36, 37, 38, 39, 40, 41, 42, 43, 44, 45, 56, 47, 48, 49, 50, 51, 52, 53, or 54 IU/kg once weekly, e.g., about 41 IU/kg once weekly, the subject's ABR is reduced, relative to the average ABR upon episodic or on demand treatment, by between about 70% and about 90%, e.g., the ABR is reduced by between about 76% and about 89%, e.g., the ABR is reduced by about 70%, about 75%, about 76%, about 77%, about 78%, about 79%, about 80%, about 81%, about 82%, about 83%, about 84%, about 85%, about 86%, about 87%, about 88%, about 89%, or about 90%, e.g., the ABR is reduced by about 83%.

In certain embodiments where a hemophilia B subject is treated prophylactically via a fixed dose at an individualized interval, e.g., about 100 IU/kg administered between about every 10 days and about every 14 days, e.g., every 10 days, every 11 days, every 12 days, every 13 days, or every 14 days, e.g., or about every 13 days, the subject's ABR is reduced, relative to the average ABR upon episodic or on demand treatment, by between about 80% and about 95%, e.g., e.g., the ABR is reduced by between about 80% and about 92%, e.g., the ABR is reduced by about 80%, about 81%, about 82%, about 83%, about 84%, about 85%, about 86%, about 87%, about 88%, about 89%, about 90%, about 91%, about 92%, about 93%, about 94%, or about 95%, e.g., about 87%.

In certain embodiments, prophylactic treatment of a hemophilia B subject with rFIXFBP by a fixed dose at a fixed interval, a fixed dose at an individualized interval, an individualized dose at a fixed interval, or an individualized dose at an individualized interval can achieve an ABR of less than 1, less than two, less than three, less than 4, or less than 5 bleeding episodes per year, e.g., between about 1 and about 5 bleeding episodes per year.

In other embodiments, the dosing amount (or ranges of the dosing amount) and the dosing interval (or ranges of the dosing interval) of a rFIXFBP polypeptide stops on-going, uncontrollable bleeding or bleeding episodes in a subject administered with the dosing amount during the dosing interval. In still other embodiments, the dosing amount (or ranges of the dosing amount) and the dosing interval (or ranges of the dosing interval) of a rFIXFBP polypeptide prevents spontaneous bleeding or bleeding episodes in a subject susceptible to such spontaneous bleeding or bleeding episodes. Various dosing amounts and dosing intervals are described in International Appl. No. PCT/US2011/043569 filed Jul. 11, 2011 and published as WO 2012/006624 on Jan. 12, 2012, which is incorporated herein by reference in its entirety.

In one aspect, this disclosure provides a method of administering a rFIXFBP polypeptide to a hemophilia B subject in need of prophylaxis, comprising intravenously administering to the subject a pharmaceutical composition as disclosed herein, e.g., reconstituted from one or more pharmaceutical kits provided herein, at an initial dose of about 50 IU/kg, administered about once per week, e.g., about once every seven days, which can include, e.g., every 6, 7, or 8 days. According to this aspect, the administration can prevent or reduce the frequency of bleeding episodes in the subject. In a further aspect, this disclosure provides a method of administering a rFIXFBP polypeptide to a hemophilia B subject in need of prophylaxis, comprising intravenously administering to the subject a pharmaceutical composition as disclosed herein, e.g., reconstituted from one or more pharmaceutical kits provided herein, at an initial dose of about 100 IU/kg, administered once every 10 to 14 days, e.g., about once every 10, 11, 12, 13, or 14 days. According to this aspect, the administration can prevent or reduce the frequency of bleeding episodes in the subject. As a further aspect of either of these methods, the prophylactic dose amount or dose frequency can be subsequently adjusted based on the subject's response, measured e.g., by the one stage clotting assay (activated partial thromboplastin time; aPTT), the thrombin generation time assay (TGA), or rotational thromboelastometry assay (ROTEM®). Those of ordinary skill in the art, e.g., physicians treating hemophilia B subjects can easily envision how, and to what degree a subject's dose or dose frequency should be adjusted in order to proactively prevent and/or reduce bleeding episodes in the subject.

In one aspect, this disclosure provides a method of administering a rFIXFBP polypeptide to a hemophilia B subject in need of treatment of a minor to moderate bleeding episode, comprising intravenously administering to the subject a pharmaceutical composition as disclosed herein, e.g., reconstituted from one or more pharmaceutical kits provided herein, at an initial dose of about 30 IU/kg to about 60 IU/kg, e.g., 30 IU/kg, 40 IU/kg, 50 IU/kg, or 60 IU/kg. According to this aspect, the administration can control, alleviate, or reverse the bleeding episode. The method can further comprise administering one or more additional doses, with the first additional dose administered in about 48 hours, and subsequent doses administered every 48 hours, if the subject exhibits further evidence of bleeding. Administration can continue according to this aspect until the bleeding episode has subsided. A person of ordinary skill in the art, e.g., a physician treating hemophilia B subjects can determine the initial dose based on the severity of the bleeding episode, the subject's response, and by the level of FIX activity in the subject's blood.

In one aspect, this disclosure provides a method of administering a rFIXFBP polypeptide to a hemophilia B subject in need of treatment of a major bleeding episode, comprising intravenously administering to the subject a pharmaceutical composition as disclosed herein, e.g., reconstituted from one or more pharmaceutical kits provided herein, at an initial dose of about 100 IU/kg. According to this aspect, the administration can control, alleviate, or reverse the bleeding episode. The method can further comprise administering an additional dose of about 80 IU/kg after about 6 to 10 hours if the bleeding episode continues. The method can further comprise administering one or more additional doses of about 80 IU/kg about every 24 hours for three days if the bleeding episode continues. The method can further comprise administering one or more additional doses of 80 IU/kg every 48 hours until the bleeding episode is controlled. Administration can continue according to this aspect until the bleeding episode has subsided.

In one aspect, this disclosure provides a method of administering a rFIXFBP polypeptide to a hemophilia B subject in need of surgical prophylaxis, comprising intravenously administering to a subject undergoing minor surgery, e.g., an uncomplicated dental extraction, a pharmaceutical composition as disclosed herein, e.g., reconstituted from one or more pharmaceutical kits provided herein, at a dose of about 50 IU/kg to about 80 IU/kg, e.g., 50 IU/kg, 60 IU/kg, 70 IU/kg, or 80 IU/kg, to be administered perioperatively, i.e., before, concurrently with, or after an minor operative procedure. According to this aspect, the administration can control bleeding in the subject during and after surgery. The method can further comprise administering an additional dose of about 50 IU/kg to about 80 IU/kg at about 24 to about 48 hours after surgery if needed to control post-operative bleeding.

In one aspect, this disclosure provides a method of administering a rFIXFBP polypeptide to a hemophilia B subject in need of surgical prophylaxis, comprising intravenously administering to a subject undergoing major surgery a pharmaceutical composition as disclosed herein, e.g., reconstituted from one or more pharmaceutical kits provided herein, at a dose of about 100 IU/kg administered perioperatively, i.e., before, concurrently with, or after a major operative procedure. According to this aspect, the administration can control bleeding in the subject during and after surgery. Major surgeries can include without limitation, total knee replacement, an arthroscopic procedure, e.g., an arthroscopic ankle fusion, a close of a rectal fistula, an external fixation of a knee, a tendon transfer, incision and drainage of a dental abscess with extractions, incision and drainage of a pilonidal cyst, debridement, partial amputation, or amputation of a finger. The method can further comprise administering an additional dose of about 80 IU/kg after about 6 to 10 hours if needed to control post-operative bleeding. The method can further comprise administering one or more additional doses of about 80 IU/kg about every 24 hours for three days if the bleeding episode continues. The method can further comprise administering one or more additional doses of 80 IU/kg every 48 hours until the bleeding episode is controlled. Administration can continue according to this aspect until the bleeding episode has subsided.

In one aspect, this disclosure provides pharmacokinetic parameters of the pharmaceutical composition provided herein, in comparison with commercially-available rFIX (a polypeptide consisting of full-length mature Factor IX, e.g., BENEFIX®).

In one embodiment the pharmaceutical composition provided herein has a mean $T_{1/2beta}$ (activity) of about 70 hours to about 95 hours, e.g., a mean $T_{1/2beta}$ (activity) of about 82 hours following a single IV infusion of 50 IU/kg rFIXFBP. In certain embodiments, the pharmaceutical composition provided herein, administered as a single IV infusion of 50 IU/kg rFIXFBP, has a mean $T_{1/2beta}$ (activity) is at least about 2-fold to about 3-fold higher than BENEFIX®, e.g., the mean $T_{1/2beta}$ (activity) is about 2.4-fold higher than BENEFIX®, following a single IV infusion of 50 IU/kg BENEFIX®.

In one embodiment the pharmaceutical composition provided herein has a has a mean $C_{max}$ of about 30 IU/dL to about 50 IU/dL, e.g., about 40.8 IU/dL, following a single IV infusion of 50 IU/kg rFIXFBP. In one embodiment the pharmaceutical composition provided herein has a has a mean area under the curve per dose (AUC/Dose) of about 27 IU*h/dL per IU/kg to about 35 IU*h/dL per IU/kg, e.g., about 31.32 IU*h/dL per IU/kg, following a single IV infusion of 50 IU/kg rFIXFBP. In certain embodiments, the pharmaceutical composition provided herein, administered as a single IV infusion of 50 IU/kg rFIXFBP, has a mean AUC/Dose at least about 1.8-fold to about 2.1-fold, e.g., about 1.99-fold higher than BENEFIX®, following a single IV infusion of 50 IU/kg BENEFIX®.

In certain embodiments of the invention, the method of the invention further comprises measuring a baseline FIX activity of a subject prior to the initial administration of a rFIXFBP polypeptide. Measuring of a baseline FIX activity can employ any known clotting assays in the art, e.g., one step aPTT assay, two step chromogenic assay, ROTEM, TGA, or etc.

In some embodiments, the method of the invention further comprises measuring a $T_{1/2beta}$ (activity) or $T_{1/2beta}$ (antigen) of the rFIXFBP polypeptide in the subject after administration of a rFIXFBP polypeptide.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1. Product Description rFIXFc is a long-acting, fully recombinant fusion protein consisting of human coagulation Factor IX (FIX) covalently linked to the Fc domain of human immunoglobulin G1 (IgG1). The Factor IX portion of rFIXFc has a primary amino acid sequence that is identical to the Thr[148] allelic form of plasma derived Factor IX and has structural and functional characteristics similar to endogenous Factor IX. The Fc domain of rFIXFc contains the hinge, CH2 and CH3 regions of IgG1. rFIXFc contains 869 amino acids with a molecular weight of approximately 98 kilodaltons.

rFIXFc is produced by recombinant DNA technology in a human embryonic kidney (HEK) cell line, which has been extensively characterized. The cell line expresses rFIXFc into a defined cell culture medium that does not contain any proteins derived from animal or human sources. rFIXFc is purified by a series of chromatography steps that does not require use of a monoclonal antibody. The process includes multiple viral clearance steps including 15 nm virus-retaining nano-filtration. No human or animal additives are used in the cell culture, purification, and formulation processes.

rFIXFc is in the pharmacotherapeutic group: antihemorrhagics, B02BD04. It is provided as a sterile, preservative-free, non-pyrogenic, lyophilized, white to off-white powder to cake, for intravenous (IV) administration in a single-use vial, accompanied by a liquid diluent in a pre-filled syringe. In addition to rFIXFc, the pharmaceutical composition comprises in the lyophilzate Sucrose, L-Histidine, Mannitol, and Polysorbate 20, and comprising in a sterile solvent Sodium Chloride Solution (0.325%). Each single-use vial contains nominally 250, 500, 1000, 2000, or 3000 International Units (IU) of rFIXFc. When reconstituted with provided diluent, the product contains the following excipients: sucrose, sodium chloride, L-histidine, mannitol, and polysorbate 20, at the concentrations shown in Table 1 or Table 2 below. The pharmaceutical composition is formulated for intravenous administration only after reconstitution.

Each pack contains a powder vial (type 1 glass) with a stopper (butyl) and a flip-off seal (aluminum), 5 ml solvent in a pre-filled syringe (type 1 glass) with a plunger stopper (butyl), a tip-cap (butyl), and a sterile vial adapter reconstitution device.

TABLE 1

| | | rFIXFc Formulations | | | |
|---|---|---|---|---|---|
| rFIXFc IU/ml* | % (w/v) Sucrose | % (w/v) Mannitol | NaCl (mM) | L-histidine (mM) | % (w/v) Polysorbate-20 |
| 50 IU/ml | 1.2 | 2.4 | 55.6 | 25 | 0.010 |
| 100 IU/ml | 1.2 | 2.4 | 55.6 | 25 | 0.010 |
| 200 IU/ml | 1.2 | 2.4 | 55.6 | 25 | 0.010 |
| 400 IU/ml | 1.2 | 2.4 | 55.6 | 25 | 0.010 |
| 600 IU/ml | 1.7 | 3.3 | 55.6 | 35 | 0.014 |

TABLE 2

| | rFIXFc Formulations | | | | |
|---|---|---|---|---|---|
| | Concentration | | | | |
| Component | 250 IU/vial | 500 IU/vial | 1000 IU/vial | 2000 IU/vial | 3000 IU/vial |
| rFIXFc* | 50 IU/mL | 100 IU/mL | 200 IU/mL | 400 IU/mL | 600 IU/mL |
| L-Histidine | 3.88 mg/mL | 3.88 mg/mL | 3.88 mg/mL | 3.88 mg/mL | 5.43 mg/mL |
| Mannitol | 23.8 mg/mL | 23.8 mg/mL | 23.8 mg/mL | 23.8 mg/mL | 33.3 mg/mL |
| Sucrose | 11.9 mg/mL | 11.9 mg/mL | 11.9 mg/mL | 11.9 mg/mL | 16.7 mg/mL |
| Polysorbate 20 | 0.10 mg/mL | 0.10 mg/mL | 0.10 mg/mL | 0.10 mg/mL | 0.14 mg/mL |
| NaCl | 3.25 mg/mL | 3.25 mg/mL | 3.25 mg/mL | 3.25 mg/mL | 3.25 mg/mL |
| Water for Injection | | | 5 mL | | |

*The potency (IU) is determined using One Stage Activated Partial Thromboplastin Time (aPTT) as per Ph. Eur 2.7.11 and USP <32> against an in-house standard that is referenced to the WHO concentrate standard. The specific activity of rFIXFc is ≥55 IU/mg protein.

Example 2: Method of Formulation

The rFIXFc drug product is a sterile lyophilized powder for injection intended for intravenous administration. It is supplied in aseptically filled single use vials which contain nominally 250, 500, 1000, 2000, and 3000 IU per vial. The vials are 10 mL USP/Ph. Eur. Type 1 glass vials sealed with a 20 mm Teflon-coated butyl rubber lyophilization stopper and aluminum flip-off crimp seal. Prior to lyophilization, the nominal fill volume target for 250 through 2000 IU vials is 5 mL and 7 mL for the 3000 IU vial. The composition of the formulation excipients prior to lyophilization is the same for all dosage strengths. The powder for injection is reconstituted with 5 mL of diluent comprising 0325% (w/v) sodium chloride supplied in a sterile prefilled syringe.

The compositions of the drug product solutions prior to lyophilization are presented in Table 3. and composition of the lyophilized powders are presented in Table 4. The compositions of the drug products following reconstitution are presented in Table 1 or in Table 2. (Example 1).

TABLE 3 rFIXFc Powder for Injection Composition Per mL Prior to Lyophilization

| | | Quantity[i] | | | | |
|---|---|---|---|---|---|---|
| Component | Function | 250 IU Vial | 500 IU Vial | 1000 IU Vial | 2000 IU Vial | 3000 IU vial |
| rFIXFc | Active ingredient | 50 IU | 100 IU | 200 IU | 400 IU | 429 IU |
| L-Histidine[ii] | Buffer | 3.88 mg | 3.88 mg | 3.88 mg | 3.88 mg | 3.88 mg |
| D-Mannitol | Bulking agent | 23.8 mg | 23.8 mg | 23.8 mg | 23.8 mg | 23.8 mg |
| Sucrose | Stabilizer | 11.9 mg | 11.9 mg | 11.9 mg | 11.9 mg | 11.9 mg |
| Polysorbate 20 | Stabilizer | 0.10 mg | 0.10 mg | 0.10 mg | 0.10 mg | 0.10 mg |
| Water for Injection | Solvent | QS to 1 mL | | | | |

[i]Amounts are nominal.
[ii]Small amounts of Hydrochloric Acid and/or Sodium Hydroxide are added during compounding to adjust the pH to 7.1.

TABLE 4

Nominal rFIXFc Powder for Injection Composition Per Vial

| | | Quantity[i] | | | | |
|---|---|---|---|---|---|---|
| Component | Function | 250 IU Vial | 500 IU Vial | 1000 IU Vial | 2000 IU Vial | 3000 IU Vial |
| rFIXFc | Active ingredient | 250 IU | 500 IU | 1000 IU | 2000 IU | 3000 IU |
| L-Histidine[ii] | Buffer | 19.4 mg | 19.4 mg | 19.4 mg | 19.4 mg | 27.2 mg |
| Mannitol | Stabilizer/bulking agent | 119 mg | 119 mg | 119 mg | 119 mg | 167 mg |
| Sucrose | Stabilizer/bulking agent | 59.5 mg | 59.5 mg | 59.5 mg | 59.5 mg | 83.3 mg |
| Polysorbate 20 | Stabilizer | 0.5 mg | 0.5 mg | 0.5 mg | 0.5 mg | 0.7 mg |

Administration can be carried out by attaching the syringe to a standard IV-infusion tubing/needle set, and delivering the rFIXFc intravenously by standard methods known to those of ordinary skill in the art.

Example 3: Dosage and Method of Administration/Method of Calculating Initial Estimated Dose rFIXFc is long-acting anti-hemophilic factor (recombinant) indicated in adults and children (≥12 years) with hemophilia B (congenital Factor IX deficiency) for, e.g., control and prevention of bleeding episodes, routine prophylaxis to prevent or reduce the frequency of bleeding episodes, and perioperative management (surgical prophylaxis).

Dosing of rFIXFc, formulated as described in Example 1, can be estimated as described in this example, but can also be determined by standard tests such as FIX activity assays described elsewhere herein.

1 IU of rFIXFc per kg body weight is expected to increase the circulating level of Factor IX by 1% [IU/dL]. rFIXFc has been shown to have a prolonged circulating half-life.

No dose adjustment for recovery is generally required. Since subjects may vary in their pharmacokinetic (e.g., half-life, in vivo recovery) and clinical responses to rFIXFc, the expected in vivo peak increase in Factor IX level expressed as IU/dL (or % of normal) or the required dose can be estimated using the following formulas:

IU/dL (or % of normal)=[Total Dose (IU)/body weight (kg)]×recovery (IU/dL per IU/kg)

OR

Dose (IU)=body weight (kg)×Desired Factor IX Rise (IU/dL or % of normal)×reciprocal of recovery (IU/kg per IU/dL)

The following table (Table 5) can be used to guide dosing in bleeding episodes:

TABLE 5

Guide to rFIXFc Dosing for Treatment of Bleeding

| Severity of Bleed | Factor IX Level Required (IU/dL or % of normal) | Dose (IU/kg)/Frequency of Doses (hrs) |
|---|---|---|
| Minor and Moderate For example: joint, superficial muscle/no neurovascular compromise | 30-60 | 30-60 IU/kg Repeat every 48 hours if there is further evidence of bleeding |

TABLE 5-continued

Guide to rFIXFc Dosing for Treatment of Bleeding

| Severity of Bleed | Factor IX Level Required (IU/dL or % of normal) | Dose (IU/kg)/Frequency of Doses (hrs) |
|---|---|---|
| (except iliopsoas), superficial soft tissue, mucous membranes | | |
| Major For example: iliopsoas and deep muscle with neurovascular injury, or substantial blood loss, retroperitoneum, CNS | 80-120 | For repeat dosing, follow guidelines for major surgery [see Table 6] |

Adapted from: Roberts and Eberst, WFH 2008, and WFH 2012

Subsequent dosage and duration of treatment depends on the individual clinical response, the severity of the Factor IX deficiency, and the location and extent of bleeding (see pharmacokinetics in Example 5 below).

The following table (Table 6) can be used to guide dosing for and perioperative management (surgical prophylaxis):

TABLE 6

Guide to rFIXFc Dosing for Perioperative Management (Surgical Prophylaxis)*

| Type of Surgery | Initial Factor IX Level Required (IU/dL or % of normal) | Dose (IU/kg)/Frequency of Doses (hrs) |
|---|---|---|
| Minor Minor operations including uncomplicated dental extraction | 50 to 80 | 50-80 IU/kg A single infusion may be sufficient. Repeat as needed after 24-48 hours. |
| Major | 60 to 120 (initial level) Days 1-3: maintain level 40-60% Days 4-6: maintain level 30-50% Days 7-14: maintain level 20-40% | 100 IU/kg (initial dose) A repeat dose at 80 IU/kg should be considered after 6-10 hours and then every 24 hours for the first 3 days. Based on the long half-life of rRIXFc, the dose may be reduced and frequency of dosing in the post-surgical setting may be extended after day 3 to every 48 hours. |

Adapted from: Roberts and Eberst, WFH 2008, and WFH 2012
*See Pharmacokinetics (Example 5 below)

For routine prophylaxis, The recommended starting regimens are either: 50 IU/kg once weekly, or 100 IU/kg once every 10-14 days. Either regimen can be adjusted based on subject response (see Pharmacokinetics, Example 5 below).

rFIXFc is contraindicated in subjects who have manifested severe hypersensitivity reactions, including anaphylaxis, to the product or its components.

The clinical response to rFIXFc may vary. If bleeding is not controlled with the recommended dose, the plasma level of Factor IX can be determined, and a sufficient dose of rFIXFc can be administered to achieve a satisfactory clinical response. If the subject's plasma Factor IX level fails to increase as expected or if bleeding is not controlled after rFIXFc administration, the subject's plasma can be tested for the presence of an inhibitor, e.g., neutralizing antibodies. Subjects using rFIXFc can be monitored for the development of Factor IX inhibitors by appropriate clinical observations and laboratory tests known to those of ordinary skill in the art.

Subject's plasma can be monitored for Factor IX activity levels by performing, e.g., the one-stage clotting assay to confirm adequate Factor IX levels have been achieved and maintained, when clinically indicated. Subject's plasma can further be monitored for the development of Factor IX inhibitors.

Example 4: B-LONG Study Design

Design is Global, Open-Label, Multicenter, Phase 3 Study
Objectives is to evaluate the efficacy and safety of intravenously-injected recombinant Factor IX Fc fusion protein (rFIXFc) in the control and prevention of bleeding episodes, routine prophylaxis, and perioperative management in individuals with severe hemophilia B.

Key inclusion criteria (a) male, (b) older than 12 years of age, (c) having diagnosis of severe hemophilia B defined as ≤2% (≤2 IU/dL FIX:C) endogenous Factor IX activity, and (d) having history of ≥100 prior documented exposure days with any currently marketed FIX product.

Treatment arms include Arm 1 (weekly prophylaxis), Arm 2 (individualized interval prophylaxis), Arm 3 (episodic [on-demand] treatment), and Arm 4 (perioperative management).

Under Arm 1 (weekly prophylaxis), subjects were treated weekly with an initial dose of 50 IU/kg, which was subsequently adjusted to maintain trough factor levels sufficient to prevent bleeding.

Under Arm 2 (individualized interval prophylaxis), subjects were treated with 100 IU/kg, at an initial interval of 10 days, which was subsequently adjusted to maintain trough factor levels sufficient to prevent bleeding.

Under Arm 3 (episodic [on-demand] treatment), subjects received rFIXFc episodic treatment as needed for bleeding.

Under Arm 4 (perioperative management), rFIXFc was administered prior to and following major surgery; subjects were allowed to enroll directly into the surgery arm, and then move into one of the treatment arms (Arm 1, Arm 2, or Arm 3) post-surgery; or to move into the surgery arm from another arm during the perioperative period if they required a surgery during the study.

For PK Assessment, all subjects in all arms had an initial PK assessment after their first dose of rFIXFc. A subset of subjects from Arm 1 were assigned to a protocol-specified sequential PK subgroup to compare the PK of rFIXFc with recombinant Factor IX (rFIX, BENEFIX®) as follows: (1) prior to treatment in Arm 1, PK was assessed after a single dose of BENEFIX® 50 IU/kg. PK was then assessed in these same subjects after a single dose of rFIXFc 50 IU/kg; and (2) PK of rFIXFc was repeated at Week 26. Key efficacy outcome measures include (1) annualized bleeding rate (ABR) in Arms 1, 2, and 3 ((i) weekly prophylaxis arm compared with the episodic treatment arm, and (ii) individualized interval prophylaxis arm compared with the episodic treatment arm); (2) number of injections required to stop a bleeding episode; and (3) treating physicians' assessments of subjects' response to surgery with rFIXFc using a 4-point scale.

Pharmacokinetic (PK) outcome measures include PK of rFIXFc and recombinant Factor IX (rFIX, BENEFIX®).

Key safety outcome measures include (a) incidence of inhibitor development and (b) incidence of adverse events (AEs) occurring outside of the perioperative management arm (Arms 1, 2, and 3 but not 4)

B-LONG Results
Subjects

The safety, efficacy and pharmacokinetics of rFIXFc was evaluated in a multicenter, open-label, prospective study that compared the efficacy of each of 2 prophylactic treatment regimens to episodic (on-demand) treatment; determined hemostatic efficacy in the treatment of bleeding episodes; and determined hemostatic efficacy during perioperative management of subjects undergoing major surgical procedures. A total of 123 previously treated subjects (PTPs) aged 12-71 with severe hemophilia B (≤2% endogenous FIX activity) were followed for up to 77 weeks. 93.5% of subjects completed the study, with 115 subjects treated at least 26 weeks and 56 subjects treated for at least 52 weeks.

Sixty-three (63) subjects in the fixed weekly interval arm received rFIXFc for routine prophylaxis starting at an initial dose of 50 IU/kg. The dose was adjusted to maintain trough between 1 and 3% above baseline or higher as clinically indicated to prevent bleeding. The median weekly dose during the last 6 months on study in 58 subjects who were on study for at least 9 months was 40.7 IU/Kg (interquartile range, 32.3, 54.1).

Twenty-nine (29) subjects in the individualized interval arm received rFIXFc for routine prophylaxis at a dose of 100 IU/kg every 10 days, with the interval adjusted to maintain trough between 1 and 3% above baseline or higher as clinically indicated to prevent bleeding. The median interval during the last 6 months in 26 subjects who were on study for at least 9 months was 13.8 days (interquartile range, 10.5, 14.0).

Twenty-seven (27) subjects received rFIXFc as needed for the treatment of bleeding episodes in the episodic (on-demand) treatment arm.

Twelve (12) subjects received rFIXFc for perioperative management in 14 major surgical procedures. Four subjects did not participate in the other arms.

Efficacy in Routine Prophylaxis

There was a reduction in annualized bleed rate (ABR) of 83% (76% to 89%) for subjects in the fixed weekly interval arm and a reduction of 87% (80% to 92%) for subjects in the individualized interval treatment arm compared to the episodic (on-demand) treatment arm based on a negative binomial model.

The median duration of treatment on study was 51.4 weeks (range <1-77). A comparison of the ABRs in subjects evaluable for efficacy is summarized in Table 7.

TABLE 7

Summary of Median (IQR*) Annualized Bleed Rate (ABR) by Treatment Arm

| Bleeding Episode Etiology | Prophylaxis Fixed Weekly Interval (N = 61) | Prophylaxis Individualized Interval (N = 26) | Episodic (On Demand) (N = 27) |
|---|---|---|---|
| Median Overall ABR (IQR) | 2.95 (1.01, 4.35) | 1.38 (0.00, 3.43) | 17.69 (10.77, 23.24) |
| Median Spontaneous ABR (IQR) | 1.04 (0.00, 2.19) | 0.88 (0.00, 2.30) | 11.78 (2.62, 19.78) |
| Median Traumatic ABR (IQR) | 0.99 (0.00, 2.13) | 0.00 (0.00, 0.78) | 2.21 (0.00, 6.81) |

*IQR = interquartile range

Efficacy in Control of Bleeding

A total of 636 bleeding events were observed in the fixed dose, fixed interval, and the episodic (on-demand) arms. Assessment of response to each injection was recorded by subjects at 8-12 hours post-treatment. Bleeding episodes are summarized in Table 8.

TABLE 8

Summary of Efficacy in Control of Bleeding

| New Bleeding episodes | (N = 636) |
|---|---|
| # of Injections to treat bleeding episodes | |
| 1 injection | 575 (90.4%) |
| 2 injections | 44 (6.9%) |
| 3 injections | 17 (2.7%) |
| Median dose per injection (IU/kg) to treat a bleeding episode (IQR) | 46.07 (32.86, 57.03) |
| Median total dose (IU/kg) to treat a bleeding episode (IQR) | 46.99 (33.33, 62.50) |
| Response to first injection | (N = 613) |
| Excellent or good | 513 (83.7%) |
| Moderate | 90 (14.7%) |
| No response | 10 (1.6%) |

Efficacy in Perioperative Management (Surgical Prophylaxis)

Fourteen (14) major surgical procedures were performed in 12 subjects. Hemostasis was assessed at 24 hours post-operatively by the investigator using a 4-point scale of excellent, good, fair, and none. The hemostatic response was rated as excellent or good in 100% of major surgeries. There was no clinical evidence of thrombotic complications in any of the subjects. Hemostatic response to dosing during surgery and post-operatively is summarized in Table 9.

TABLE 9

Summary of Hemostatic Response During Surgery and Post-Operatively

| Major Surgery | Number of Procedures (Number of Subjects) | Response | | | |
|---|---|---|---|---|---|
| | | Excellent | Good | Fair | Poor/None |
| Total Knee Replacement | 5 (5) | 4 | 1 | | |
| Arthroscopic Procedure | 1 (1) | 1 | | | |
| Arthroscopic Ankle Fusion | 1 (1) | 1 | | | |
| Closure of Rectal Fistula | 1 (1) | 1 | | | |
| External Fixation of Knee | 1 (1) | 1 | | | |
| Tendon Transfer | 1 (1) | 1 | | | |
| I & D[1] of Dental Abscess with Extractions | 1 (1) | 1 | | | |
| I & D[1] Pilonidal Cyst | 1 (1) | 1 | | | |
| Debridement, Partial Amputation | 1 (1) | 1 | | | |
| Amputation of Finger | 1 (1) | 1 | | | |
| Minor surgery[2] | 15 (13) | 10 | 1 | 1 | |

[1]Incision and Drainage
[2]Assessment of response not provided for 3 minor surgeries Impact on Quality of Life Quality of Life was measured using the HAEM-A-QoL, a quality of life instrument specific to hemophilia. HAEM-A-QoL was performed in adults (aged 18 and older) in the prophylactic treatment arms. Change from baseline at Week 26 in the combined prophylaxis arms by pre-study regimen are summarized in Table 10.

TABLE 10

Median Change from Baseline for the Haem-A-QoL Questionnaire (Fixed Weekly Interval and Individualized Interval Arms Pooled)

|  | Pre-Study Regimen | | | | |
|---|---|---|---|---|---|
|  | Prophylaxis | | Episodic (On-demand) | | |
|  | N | Change from baseline | N | Change from baseline | |
| Total score | 27 | −6.82 (−22.8, 6.1) | 26 | −6.25 (−25.5, 12.8) | |
| Domains, during the past month | | | | | |
| 1. Physical health | 27 | −10.00 (−45.0, 20.0) | 31 | −15.00 (−60.0, 15.0) | |
| 2. Feeling | 27 | 0.00 (−43.8, 50.0) | 31 | 0.00 (−43.8, 62.5) | |
| 3. View of yourself | 27 | −5.00 (−25.0, 15.0) | 30 | −5.00 (−35.0, 25.0) | |
| 4. Sports and leisure | 22 | −7.50 (−70.0, 25.0) | 21 | −20.00 (−40.0, 35.0) | |
| 5. Work and school | 22 | 0.00 (−31.3, 52.1) | 25 | −6.25 (−31.3, 18.8) | |
| 6. Dealing with hemophilia | 27 | 0.00 (−100.0, 100.0) | 31 | −8.33 (−66.7, 75.0) | |
| 7. Treatment | 27 | −6.25 (−18.8, 18.8) | 31 | 0.00 (−53.1, 37.5) | |
| Domains, recently | | | | | |
| 8. Future | 26 | −5.00 (−25.0, 10.0) | 30 | 0.00 (−30.0, 20.0) | |
| 9. Family planning | 15 | 0.00 (−29.2, 12.5) | 13 | 0.00 (−43.8, 25.0) | |
| 10. Partnership and sexuality | 26 | 0.00 (−50.0, 66.7) | 30 | 0.00 (−25.0, 25.0) | |

NOTE:
Summary statistics are median (minimum, maximum).

The median dosing interval in the individualized interval prophylaxis arm was 14 days during the last 6 months on study.

Control of bleeding: Over 90% (90.4%) of bleeding episodes were controlled by a single injection of rFIXFc.

Perioperative management: Treating physicians rated the hemostatic efficacy of rFIXFc as excellent or good in 100% of surgeries.

Adverse drug reactions (ADRs) were reported in 10 of 119 (8.4%) subjects treated with routine prophylaxis or episodic (on-demand) therapy. Adverse drug reactions are considered adverse events assessed by the investigator as related or possibly related to treatment with rFIXFc. Adverse drug reactions are summarized in Table 11.

No subject was withdrawn from study due to an adverse drug reaction. In the study, no inhibitors were detected and no events of anaphylaxis were reported.

TABLE 11

Adverse Drug Reactions reported for rFIXFc

| MedDRA System Organ Class | MedDRA Preferred Term | N = 119* Number of Subjects n (%) |
|---|---|---|
| Nervous system disorders | Headache | 2 (1.7) |
|  | Dizziness | 1 (0.8) |
|  | Dysgeusia | 1 (0.8) |
| Gastrointestinal disorders | Paresthesia oral | 2 (1.7) |
|  | Breath odor | 1 (0.8) |
| General disorders and administration site conditions | Fatigue | 1 (0.8) |
|  | Infusion site pain | 1 (0.8) |
| Cardiac disorders | Palpitations | 1 (0.8) |
| Renal and urinary disorders | Obstructive uropathy | 1 (0.8) |
| Vascular disorders | Hypotension | 1 (0.8) |

*119 previously treated subjects (PTPs) on routine prophylaxis or episodic (on-demand) therapy
The incidence of the adverse reactions below is expressed according to the following categories: Very common (≥1/10) Common (≥1/100 to <1/10) Uncommon (≥1/1,000 to <1/100) Rare (≥1/10,000 to <1/1,000) Very rare (<1/10,000)

Example 5: Pharmacodynamics and Pharmacokinetics

Pharmacodynamics rFIXFc is a long-acting, fully recombinant, fusion protein that temporarily replaces the missing clotting Factor IX needed for effective hemostasis. rFIXFc contains the Fc region of human immunoglobulin G1 (IgG1) that binds to neonatal Fc receptor (FcRn), which is part of a naturally occurring pathway that delays lysosomal degradation of immunoglobulins by cycling them back into circulation, and is responsible for their long plasma half-life.

rFIXFc is a long-acting, fully recombinant, fusion protein comprising human coagulation Factor IX (FIX) covalently linked to the Fc domain of human immunoglobulin G1 (IgG1), and produced by recombinant DNA technology.

Factor IX (FIX) is an approximately 55 kDa vitamin K-dependent serine protease, which is an essential clotting factor in the coagulation cascade critical to the hemostasis process. FIX is normally converted to activated FIX (FIXa) by the activated factor VII/Tissue Factor complex or by activated factor XI. FIXa forms a complex with activated factor VIII on phospholipid surfaces to convert factor X to activated factor X, and which ultimately converts prothrombin to thrombin and leads to the formation of a fibrin clot.

Hemophilia B subjects have a deficiency of functional FIX, which results in prolonged bleeding after trauma and recurrent spontaneous bleeds into soft tissue and joints. The FIX portion of rFIXFc has similar structural and functional characteristics as endogenous FIX, and promotes hemostasis by correcting the deficiency of functional FIX.

The other portion of rFIXFc is the Fc region of human immunoglobulin G1 (IgG1) which binds with the neonatal Fc receptor (FcRn). This receptor is expressed throughout life as part of a naturally occurring pathway that protects immunoglobulins from lysosomal degradation by cycling these proteins back into circulation, resulting in their long plasma half-life.

rFIXFc is used as a replacement therapy to increase plasma levels of Factor IX activity, thereby enabling a temporary correction of the factor deficiency and correction of the bleeding tendency.

Hemophilia B is a bleeding disorder characterized by a deficiency of functional clotting Factor IX (FIX), which leads to a prolonged clotting time in the activated partial thromboplastin time (aPTT) assay, a conventional in vitro test for the biological activity of FIX. Treatment with rFIXFc can shorten the aPTT over the effective dosing period.

Pharmacokinetics

The pharmacokinetics (PK) of rFIXFc versus BENEFIX® [nonacog alfa] (rFIX) were evaluated following a 10-minute IV infusion in 22 evaluable subjects (≥19 years) from a clinical study. The subjects underwent a washout period of 5 days prior to receiving 50 IU/kg of BENEFIX®. PK sampling was conducted pre-dose followed by assessments at 8 time points up to 96 hours post-dose. Following a washout period of 120 hours (5 days), the subjects received a single dose of 50 IU/kg of rFIXFc. PK samples were collected pre-dose and then subsequently at 11 time points up to 240 hours (10 days) post-dose. A repeat PK evaluation of rFIXFc was conducted at Week 26.

PK parameters for rFIXFc were estimated based on the plasma FIX activity over time profile. For rFIXFc, the maximum activity (Cmax) was observed immediately following infusion, e.g., at 10 minutes from the start of the dosing. The geometric mean increase in circulating FIX activity from pre-infusion level was 0.92 IU/dL per IU/kg and the elimination half-life was 82 hours. This half-life is influenced by the Fc region of rFIXFc, which in animal models was shown to be mediated by the FcRn cycling pathway. The rFIXFc PK profile was stable over repeated dosing as shown by comparable PK parameters at Week 26.

A summary of PK parameters for rFIXFc and BENEFIX® are presented in Table 12.

TABLE 12

Pharmacokinetic Parameters of rFIXFc and BENEFIX ® (rFIX)

| PK Parameters[1] | rFIXFC (95% CI) N = 22 | BeneFIX ® (95% CI) N = 22 | Ratio of rFIXFc to BeneFIX ® (95% CI) N = 22 |
|---|---|---|---|
| $C_{max}$ (IU/dL) | 40.81 (33.60, 49.58) | 43.08 (36.69, 50.59) | 0.95 (0.81, 1.11) |
| AUC/Dose (IU * h/dL per IU/kg) | 31.32 (27.88, 35.18) | 15.77 (14.02, 17.74) | 1.99 (1.82, 2.17) |
| $t_{1/2\alpha}$ (h) | 5.03 (3.20, 7.89) | 2.41 (1.62, 3.59) | 2.09 (1.18, 3.68) |
| $t_{1/2\beta}$ (h) | 82.12 (71.39, 94.46) | 33.77 (29.13, 39.15) | 2.43 (2.02, 2.92) |
| CL (mL/h/kg) | 3.19 (2.84, 3.59) | 6.34 (5.64, 7.13) | 0.50 (0.46, 0.55) |
| MRT (h) | 98.60 (88.16, 110.29) | 41.19 (35.98, 47.15) | 2.39 (2.12, 2.71) |
| $V_{ss}$ (mL/kg) | 314.8 (277.8, 356.8) | 261.1 (222.9, 305.9) | 1.21 (1.06, 1.38) |
| Incremental Recovery (IU/dL per IU/kg) | 0.92 (0.77, 1.10) | 0.95 (0.81, 1.10) | 0.97 (0.84, 1.12) |

[1]PK parameters are presented in Geometric Mean (95% CI)
Abbreviations:
CI = confidence interval;
$C_{max}$ = maximum activity;
AUC = area under the FIX activity time curve;
$t_{1/2\alpha}$ = distribution half-life;
$t_{1/2\beta}$ = elimination half-life;
CL = clearance;
MRT = mean residence time;
$V_{ss}$ = volume of distribution at steady-state A population PK model was developed based on PK data from 135 subjects, from 12 to 76 years old and weighing between 45 kg and 186.7 kg, in two clinical studies (12 subjects in a phase 1/2a study and 123 subjects in a phase 3 study). The population estimate for the typical CL of rFIXFc is 2.39 dL/h, typical volume of central compartment (V1) is 71.4 dL, and Vss is 198.3 dL. The geometric mean terminal half-life of rFIXFc was approximately 82 hours, which is 2.4-fold longer than that of BENEFIX® (approximately 34 hours).

All subjects had an initial PK evaluation to characterize the PK of rFIXFc in a representative population of subjects with Hemophilia B.

More extensive PK sampling was conducted in a subset of subjects in the weekly prophylaxis arm (Arm 1) at baseline after a single dose of BENEFIX® 50 IU/kg followed by a single dose of rFIXFc 50 IU/kg. Blood samples were taken for BENEFIX® over a period of 96 hours. Blood samples were then taken for rFIXFc over a period of 240 hours. PK assessment of rFIXFc was repeated at 26 weeks.

The 100-IU/kg dose was selected based on PK results from the Phase 1/2 study, which showed this dose elevated FIX levels to approximately 100% of normal (Shapiro et al 2011). In the Phase 1/2 study, with rFIXFc 100 IU/kg (n=5), the time to FIX levels 1% above baseline was approximately 11 days, and ranged from 9 to 14 days. Based on these data, Arm 2 was designed to test whether a fixed dose of 100 IU/kg could provide protection from bleeding beyond one week.

The terminal half-life of BENEFIX® of approximately 34 hours determined in B-LONG is longer than that reported in the BENEFIX® package insert (~18 hours) as well as a number of studies (13.7 to 19.3 hours) (Ewenstein 2002; Kisker et al. 2003; Negrier et al. 2011) that followed EMA guidelines on FIX PK assessment using a 48-hour sampling duration. However, in published PK studies in which BENEFIX® was sampled up to 72 hours post dosing, a longer terminal half-life was also reported to be 21.3 to 33.4 hours (Ragni et al. 2002, Lambert et al. 2007, Chang et al. 2007, and Martinowitz et al. 2012).

To determine whether the discrepancy in terminal half-life of BENEFIX® resulted from the longer PK sampling schedule of 96 hours adopted in this study, BENEFIX® PK data were also analyzed using data only up to 48 hours post dose. This analysis yielded a significantly shortened terminal half-life of BENEFIX® (~17 hours) that is consistent with previous reports using 48-hour sampling duration.

In the B-LONG study, a head-to head comparison was made between rFIXFc and BENEFIX®, whereas in the Phase 1/2 study, the half-life of rFIXFc was compared to the historical data reported in the BENEFIX® Product Insert (2009). Thus, the measure of PK improvement of rFIXFC over BENEFIX® from the B LONG study is more reliable and accurate.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, used on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical composition comprising:
   (a) a rFIXFc polypeptide comprising human FIX fused to a Fc domain of a human antibody;
   (b) between about 10 mg/ml and about 20 mg/ml of sucrose;
   (c) between about 20 mg/ml and about 40 mg/ml of mannitol
   (d) between about 3 mg/ml and about 4 mg/ml of sodium chloride (NaCl);
   (e) between about 3 mg/ml and about 6 mg/ml of L-histidine; and
   (f) between about 0.08 mg/ml and about 0.2 mg/ml of polysorbate 20 or polysorbate 80.

2. The pharmaceutical composition of claim 1, comprising about 11.9 mg/ml of sucrose.

3. The pharmaceutical composition of claim 1, comprising about 16.7 mg/ml of sucrose.

4. The pharmaceutical composition of claim 1, comprising about 23.8 mg/ml of mannitol.

5. The pharmaceutical composition of claim 1, comprising about 33.3 mg/ml of mannitol.

6. The pharmaceutical composition of claim 1, comprising about 3.25 mg/ml of NaCl.

7. The pharmaceutical composition of claim 1, comprising about 3.88 mg/ml of L-histidine.

8. The pharmaceutical composition of claim 1, comprising about 5.43 mg/ml of L-histidine.

9. The pharmaceutical composition of claim 1, comprising 0.10 mg/ml of polysorbate 20 or polysorbate 80.

10. The pharmaceutical composition of claim 1, comprising about 0.14 mg/ml of polysorbate 20 or polysorbate 80.

11. The pharmaceutical composition of claim 1, comprising:
    (a) about 50 IU/ml of the rFIXFc polypeptide;
    (b) about 11.9 mg/ml of sucrose;
    (c) about 23.8 mg/ml of mannitol;
    (d) about 3.25 mg/ml of NaCl;
    (e) about 3.88 mg/ml of L-histidine; and
    (f) about 0.10 mg/ml of polysorbate 20 or polysorbate 80.

12. The pharmaceutical composition of claim 1, comprising:
    (a) about 100 IU/ml of the rFIXFc polypeptide;
    (b) about 11.9 mg/ml of sucrose;
    (c) about 23.8 mg/ml of mannitol;
    (d) about 3.25 mg/ml of NaCl;
    (e) about 3.88 mg/ml of L-histidine; and
    (f) about 0.10 mg/ml of polysorbate 20 or polysorbate 80.

13. The pharmaceutical composition of claim 1, comprising:
    (a) about 200 IU/ml of the rFIXFc polypeptide;
    (b) about 11.9 mg/ml of sucrose;
    (c) about 23.8 mg/ml of mannitol;
    (d) about 3.25 mg/ml of NaCl;
    (e) about 3.88 mg/ml of L-histidine; and
    (f) about 0.10 mg/ml of polysorbate 20 or polysorbate 80.

14. The pharmaceutical composition of claim 1, comprising:
    (a) about 400 IU/ml of the rFIXFc polypeptide;
    (b) about 11.9 mg/ml of sucrose;
    (c) about 23.8 mg/ml of mannitol;
    (d) about 3.25 mg/ml of NaCl;
    (e) about 3.88 mg/ml of L-histidine; and
    (f) about 0.10 mg/ml of polysorbate 20 or polysorbate 80.

15. The pharmaceutical composition of claim 1, comprising:
    (a) about 600 IU/ml of the rFIXFc polypeptide;
    (b) about 16.7 mg/ml of sucrose;
    (c) about 33.3 mg/ml of mannitol;
    (d) about 3.25 mg/ml of NaCl;
    (e) about 5.43 mg/ml of L-histidine; and
    (f) about 0.14 mg/ml of polysorbate 20 or polysorbate 80.

16. A pharmaceutical kit comprising:
    (a) a first container comprising a lyophilized powder, where the powder comprises
        (i) about 200 IU to about 4000 IU of a rFIXFc polypeptide comprising human Factor IX fused to a Fc domain of a human antibody;
        (ii) about 59.5 mg or about 83.3 mg of sucrose;
        (iii) about 119 mg or about 167 mg of mannitol;
        (iv) about 19.4 mg or about 27.2 mg of L-histidine; and
        (v) about 0.50 mg or about 0.7 mg of polysorbate 20 or polysorbate 80; and
    (b) a second container comprising 0.325% (w/v) NaCl to be combined with the lyophilized powder of the first container.

17. A pharmaceutical composition comprising:
    (a) between about 25 IU/ml and about 700 IU/ml of a rFIXFc polypeptide comprising human Factor IX fused to a Fc domain of a human antibody;
    (b) between about 10 mg/ml and about 20 mg/ml of sucrose;
    (c) between about 20 mg/ml and about 40 mg/ml of mannitol;
    (d) between about 3 mg/ml and about 4 mg/ml of NaCl;
    (e) between about 3 mg/ml and about 6 mg/ml of L-histidine; and
    (f) between about 0.08 mg/ml and about 0.15 mg/ml of polysorbate-20 or polysorbate-80.

18. The pharmaceutical composition of claim 17, comprising:

(a) about 50 IU/ml, about 100 IU/ml, about 200 IU/ml, or about 400 IU/ml of the rFIXFc polypeptide;
(b) about 11.9 mg/ml of sucrose;
(c) about 23.8 mg/ml of mannitol;
(d) about 3.25 mg/ml of NaCl;
(e) about 3.88 mg/ml of L-histidine; and
(f) about 0.10 mg/ml of polysorbate-20 or polysorbate-80.

19. The pharmaceutical composition of claim 17, comprising:
(a) about 600 IU/ml of the rFIXFc polypeptide;
(b) about 16.7 mg/ml of sucrose;
(c) about 33.3 mg/ml of mannitol;
(d) about 3.25 mg/ml of NaCl;
(e) about 5.43 mg/ml of L-histidine; and
(f) about 0.14 mg/ml of polysorbate-20 or polysorbate-80.

20. The pharmaceutical composition of claim 1, which is a liquid formulation.

21. A vial comprising the pharmaceutical composition of claim 20.

22. The pharmaceutical kit of claim 16, wherein the rFIXFc polypeptide comprises a first subunit comprising an amino acid sequence at least 90% identical to amino acids 1 to 642 of SEQ ID NO:2, and a second subunit comprising an amino acid sequence at least 90% identical to amino acids 1 to 227 of SEQ ID NO:4.

23. The pharmaceutical kit of claim 16, wherein the rFIXFc polypeptide is a rFIXFc polypeptide comprises a first subunit comprising amino acids 1 to 642 of SEQ ID NO:2, and a second subunit comprising amino acids 1 to 227 of SEQ ID NO:4.

24. The pharmaceutical kit of claim 22, wherein the powder comprises
(i) about 250 IU of the rFIXFc polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80.

25. The pharmaceutical kit of claim 22, wherein the powder comprises
(i) about 500 IU of the rFIXFc polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80.

26. The pharmaceutical kit of claim 22, wherein the powder comprises
(i) about 1000 IU of the rFIXFc polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80.

27. The pharmaceutical kit of claim 22, wherein the powder comprises
(i) about 2000 IU of the rFIXFc polypeptide,
(ii) about 59.5 mg of sucrose;
(iii) about 119 mg of mannitol;
(iv) about 19.4 mg of L-histidine; and
(v) about 0.50 mg of polysorbate 20 or polysorbate 80.

28. The pharmaceutical kit of claim 22, wherein the powder comprises
(i) about 3000 IU of the rFIXFc polypeptide,
(ii) about 83.3 mg of sucrose;
(iii) about 167 mg of mannitol;
(iv) about 27.2 mg of L-histidine; and
(v) about 0.7 mg of polysorbate 20 or polysorbate 80.

29. The pharmaceutical composition of claim 16, wherein the rFIXFc polypeptide comprises a first subunit comprising an amino acid sequence at least 90% identical to amino acids 1 to 642 of SEQ ID NO:2, and a second subunit comprising an amino acid sequence at least 90% identical to amino acids 1 to 227 of SEQ ID NO:4.

30. The pharmaceutical composition of claim 16, wherein the rFIXFc polypeptide comprises a first subunit comprising amino acids 1 to 642 of SEQ ID NO:2, and a second subunit comprising amino acids 1 to 227 of SEQ ID NO:4.

31. A pharmaceutical kit comprising:
(a) a first container comprising a lyophilized powder, where the powder comprises
(i) 200 IU to 4000 IU of a rFIXFc protein comprising human coagulation Factor IX (FIX) and a Fc domain of a human antibody,
wherein the rFIXFc protein comprises a first subunit comprising amino acids 1 to 642 of SEQ ID NO:2 and a second subunit comprising amino acids 1 to 227 of SEQ ID NO:4,
(ii) 59.5 mg or 83.3 mg of sucrose,
(iii) 119 mg or 167 mg of mannitol,
(iv) 19.4 mg or 27.2 mg of L-histidine, and
(v) 0.50 mg or 0.7 mg of polysorbate 20; and
(b) a second container comprising 0.325% (w/v) NaCl to be combined with the lyophilized powder of the first container.

32. The pharmaceutical kit of claim 31, wherein the powder comprises
(i) 250 IU of the rFIXFc protein;
(ii) 59.5 mg of sucrose;
(iii) 119 mg of mannitol;
(iv) 19.4 mg of L-histidine; and
(v) 0.50 mg of polysorbate 20.

33. The pharmaceutical kit of claim 31, wherein the powder comprises
(i) 500 IU of the rFIXFc protein;
(ii) 59.5 mg of sucrose;
(iii) 119 mg of mannitol;
(iv) 19.4 mg of L-histidine; and
(v) 0.50 mg of polysorbate 20.

34. The pharmaceutical kit of claim 31, wherein the powder comprises
(i) 1000 IU of the rFIXFc protein;
(ii) 59.5 mg of sucrose;
(iii) 119 mg of mannitol;
(iv) 19.4 mg of L-histidine; and
(v) 0.50 mg of polysorbate 20.

35. The pharmaceutical kit of claim 31, wherein the powder comprises
(i) 2000 IU of the rFIXFc protein;
(ii) 59.5 mg of sucrose;
(iii) 119 mg of mannitol;
(iv) 19.4 mg of L-histidine; and
(v) 0.50 mg of polysorbate 20.

36. The pharmaceutical kit of claim 31, wherein the powder comprises
(i) 3000 IU of the rFIXFc protein;
(ii) 83.3 mg of sucrose;
(iii) 167 mg of mannitol;
(iv) 27.2 mg of L-histidine; and
(v) 0.7 mg of polysorbate 20.

37. A pharmaceutical composition comprising:
(a) 25 IU/ml to 700 IU/ml of a rFIXFc protein comprising human coagulation Factor IX (FIX) and a Fc domain of a human antibody, wherein the rFIXFc protein comprises a first subunit comprising amino acids 1 to 642 of SEQ ID NO:2 and a second subunit comprising amino acids 1 to 227 of SEQ ID NO:4;
(b) 10 mg/ml to 20 mg/ml of sucrose;
(c) 20 mg/ml to 40 mg/ml of mannitol;
(d) 3 mg/ml to 4 mg/ml of NaCl;
(e) 3 mg/ml to 6 mg/ml of L-histidine; and
(f) 0.08 mg/ml to 0.15 mg/ml of polysorbate 20.

38. The pharmaceutical composition of claim 37, comprising:
(a) 50 IU/ml of the rFIXFc protein;
(b) 11.9 mg/ml of sucrose;
(c) 23.8 mg/ml of mannitol;
(d) 3.25 mg/ml of NaCl;
(e) 3.88 mg/ml of L-histidine; and
(f) 0.10 mg/ml of polysorbate 20.

39. The pharmaceutical composition of claim 37, comprising:
(a) 100 IU/ml of the rFIXFc protein;
(b) 11.9 mg/ml of sucrose;
(c) 23.8 mg/ml of mannitol;
(d) 3.25 mg/ml of NaCl;
(e) 3.88 mg/ml of L-histidine; and
(f) 0.10 mg/ml of polysorbate 20.

40. The pharmaceutical composition of claim 37, comprising:
(a) 200 IU/ml of the rFIXFc protein;
(b) 11.9 mg/ml of sucrose;
(c) 23.8 mg/ml of mannitol;
(d) 3.25 mg/ml of NaCl;
(e) 3.88 mg/ml of L-histidine; and
(f) 0.10 mg/ml of polysorbate 20.

41. The pharmaceutical composition of claim 37, comprising:
(a) 400 IU/ml of the rFIXFc protein;
(b) 11.9 mg/ml of sucrose;
(c) 23.8 mg/ml of mannitol;
(d) 3.25 mg/ml of NaCl;
(e) 3.88 mg/ml of L-histidine; and
(f) 0.10 mg/ml of polysorbate 20.

42. The pharmaceutical composition of claim 37, comprising:
(a) 600 IU/ml of the rFIXFc protein;
(b) 16.7 mg/ml of sucrose;
(c) 33.3 mg/ml of mannitol;
(d) 3.25 mg/ml of NaCl;
(e) 5.43 mg/ml of L-histidine; and
(f) 0.14 mg/ml of polysorbate 20.

* * * * *